(12) United States Patent
Aferzon et al.

(10) Patent No.: US 11,779,204 B1
(45) Date of Patent: Oct. 10, 2023

(54) INTERCHANGEABLE LENS MECHANISM FOR A HEAD-WORN DISPLAY SYSTEM AND METHOD OF ASSEMBLING THE LENS MECHANISM

(71) Applicant: Mantis Health, Inc., Stamford, CT (US)

(72) Inventors: Joshua Aferzon, Avon, CT (US); Lee Nicholson, Unionville (CA)

(73) Assignee: Mantis Health, Inc., Stamford, CT (US)

( * ) Notice: Subject to any disclaimer, the term of this patent is extended or adjusted under 35 U.S.C. 154(b) by 0 days.

(21) Appl. No.: 18/129,560

(22) Filed: Mar. 31, 2023

Related U.S. Application Data

(60) Provisional application No. 63/326,825, filed on Apr. 2, 2022.

(51) Int. Cl.

| | | |
|---|---|---|
| *A61B 3/10* | (2006.01) | |
| *A61B 3/00* | (2006.01) | |
| *A61F 2/14* | (2006.01) | |
| *G02B 27/01* | (2006.01) | |
| *G02C 7/08* | (2006.01) | |
| *G02B 7/14* | (2021.01) | |

(52) U.S. Cl.
CPC .............. *A61B 3/10* (2013.01); *A61B 3/0025* (2013.01); *G02B 7/14* (2013.01); *G02B 27/0172* (2013.01); *G02B 27/0176* (2013.01); *A61F 2/14* (2013.01); *G02B 2027/0156* (2013.01); *G02B 2027/0161* (2013.01); *G02C 7/086* (2013.01); *G02C 7/088* (2013.01)

(58) Field of Classification Search
CPC A61B 3/10; A61B 3/0025; A61F 2/14; G02B 7/14; G02B 27/0172; G02B 27/0176; G02B 2027/0156; G02B 2027/0161; G03B 17/14; G02C 7/086; G02C 7/088
See application file for complete search history.

(56) References Cited

U.S. PATENT DOCUMENTS

| | | | |
|---|---|---|---|
| 11,366,342 B2* | 6/2022 | Yonezawa | G02C 7/086 |
| 2004/0017539 A1* | 1/2004 | Nagata | G02C 7/088 |
| | | | 351/57 |
| 2019/0076013 A1* | 3/2019 | Aferzon | H04N 13/344 |
| 2020/0033560 A1* | 1/2020 | Weber | G06K 19/06028 |
| 2020/0096775 A1* | 3/2020 | Franklin | G06F 3/011 |
| 2021/0325678 A1* | 10/2021 | Maric | H04N 5/655 |

* cited by examiner

*Primary Examiner* — Collin X Beatty
(74) *Attorney, Agent, or Firm* — CALDWELL INTELLECTUAL PROPERTY LAW

(57) ABSTRACT

A lens mechanism for a head-worn display device and a method of assembling the lens mechanism is disclosed. The lens mechanism includes a first housing disposed on a head-worn display device, wherein the first housing includes a first lens display, a first optic and a first optic holder configured to rigidly maintain the first lens display and the first optic, wherein the first optic holder includes an aperture configured to allow light waves to pass from the first lens display to the first optic. The lens mechanism includes a second optic holder that includes a second optic configured for vision correction, wherein the second optic is interchangeable and located over the first optic. The second optic holder is configured to removably dispose the second optic to the head-worn display device.

18 Claims, 18 Drawing Sheets

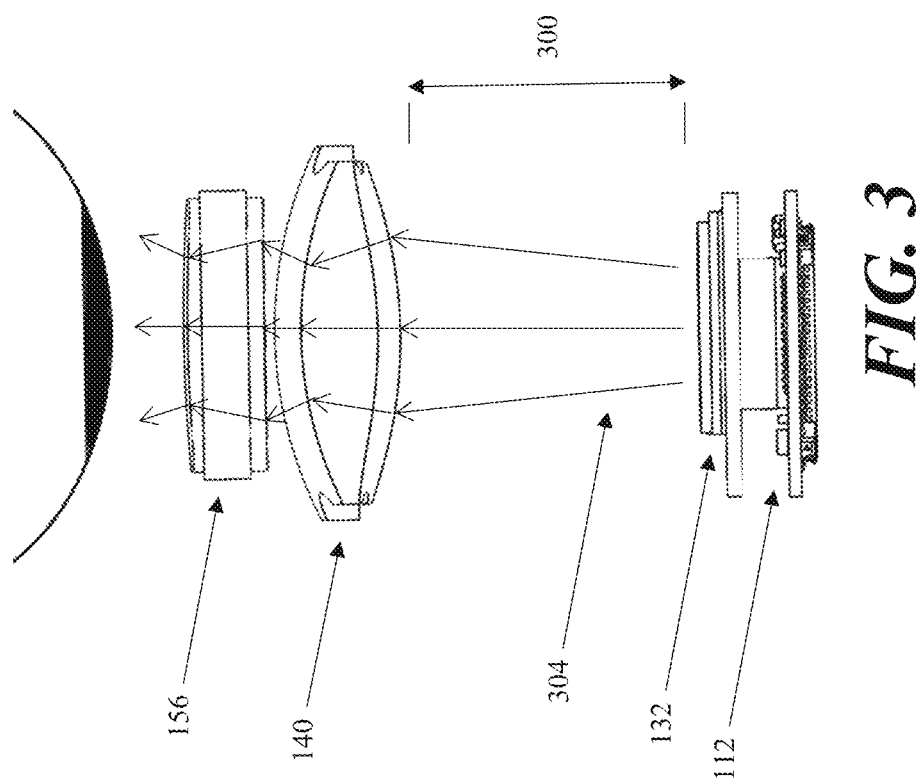

INTERCHANGEABLE LENS MECHANISM FOR A HEAD-WORN DISPLAY SYSTEM AND METHOD OF ASSEMBLING THE LENS MECHANISM

CROSS-REFERENCE TO RELATED APPLICATIONS

This application claims the benefit of priority of U.S. Provisional Patent Application Ser. No. 63/326,825, filed on Apr. 2, 2022 and titled "INTERCHANGEABLE LENS MECHANISM FOR HEAD-WORN DISPLAY SYSTEM," which is incorporated by reference herein in its entirety.

FIELD OF THE INVENTION

The present invention generally relates to the field of lens mechanisms. In particular, the present invention is directed to interchangeable lens mechanism for a head-worn display system and method of assembling the lens mechanism.

BACKGROUND

A majority of people require prescription lenses, or contact lenses, for correcting vision. There exists a challenge with vision correction to ensure proper viewing of near-eye displays that are built into head-worn display systems.

SUMMARY OF THE DISCLOSURE

In an aspect, a lens mechanism for a head-worn display device is disclosed. The lens mechanism includes a first housing disposed on a head-worn display device, wherein the first housing includes a first lens display, wherein the first lens display is configured to emit light waves to display a first image, a first optic, wherein the first optic is configured to magnify the first image of the first lens display, and a first optic holder configured to rigidly maintain the first lens display and the first optic, wherein the first optic holder includes an aperture configured to allow the light waves to pass from the first lens display to the first optic. The lens mechanism includes a second optic holder, wherein the second optic holder includes a second optic configured for vision correction, wherein the second optic is interchangeable, and the second optic is located over the first optic, and the second optic holder is configured to removably dispose the second optic to the head-worn display device.

In another aspect, a method of assembling a lens mechanism for a head-worn display device is disclosed. The method includes obtaining a first lens display configured to emit light waves to display a first image, obtaining a first optic configured to magnify the first image of the first lens display, placing the first lens display and the first optic onto a first optic holder configured to rigidly maintain the first lens display and the first optic, wherein the first optic holder includes an aperture configured to allow the light waves to pass from the first lens display to the first optic, housing the first optic, the first lens display and the first optic holder with a first housing, obtaining a head-worn display device, disposing the first housing to a first surface of the head-worn display device, wherein the first surface is distal to a user's eyes, obtaining a second optic configured for vision correction, wherein the second optic is interchangeable, disposing the second optic to a second optic holder and removably disposing the second optic holder with the second optic to a second surface of the head-worn display device over the first optic, wherein the second surface is proximal to the user's eyes.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 3 is an illustration of an exemplary embodiment of a side view of a portion of a lens mechanism;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a lens mechanism for a head-worn display device and a method of assembling the lens mechanism is disclosed. The lens mechanism includes a first housing disposed on a visor of a head-worn display device, wherein the first housing includes a first lens display, wherein the first lens display is configured to emit light waves to display at least an image, a first optic, wherein the first optic is configured to magnify the at least an image of the first lens display, and a first optic holder configured to rigidly maintain the first lens display and the first optic at a relief height, wherein the first optic holder includes an aperture configured to allow the light waves to pass from the first lens display to the first optic. The lens mechanism includes a second optic holder, wherein the second optic holder includes a second optic configured for vision correction, wherein the second optic is interchangeable, and the second optic is located over the first optic, and the second optic holder is configured to removably dispose the second optic to the visor of the head-worn display device.

Aspects of the present disclosure can be used to interchange a prescription lens to another prescription lens. Exemplary embodiments illustrating aspects of the present disclosure are described below in the context of several specific examples.

Figure 1:
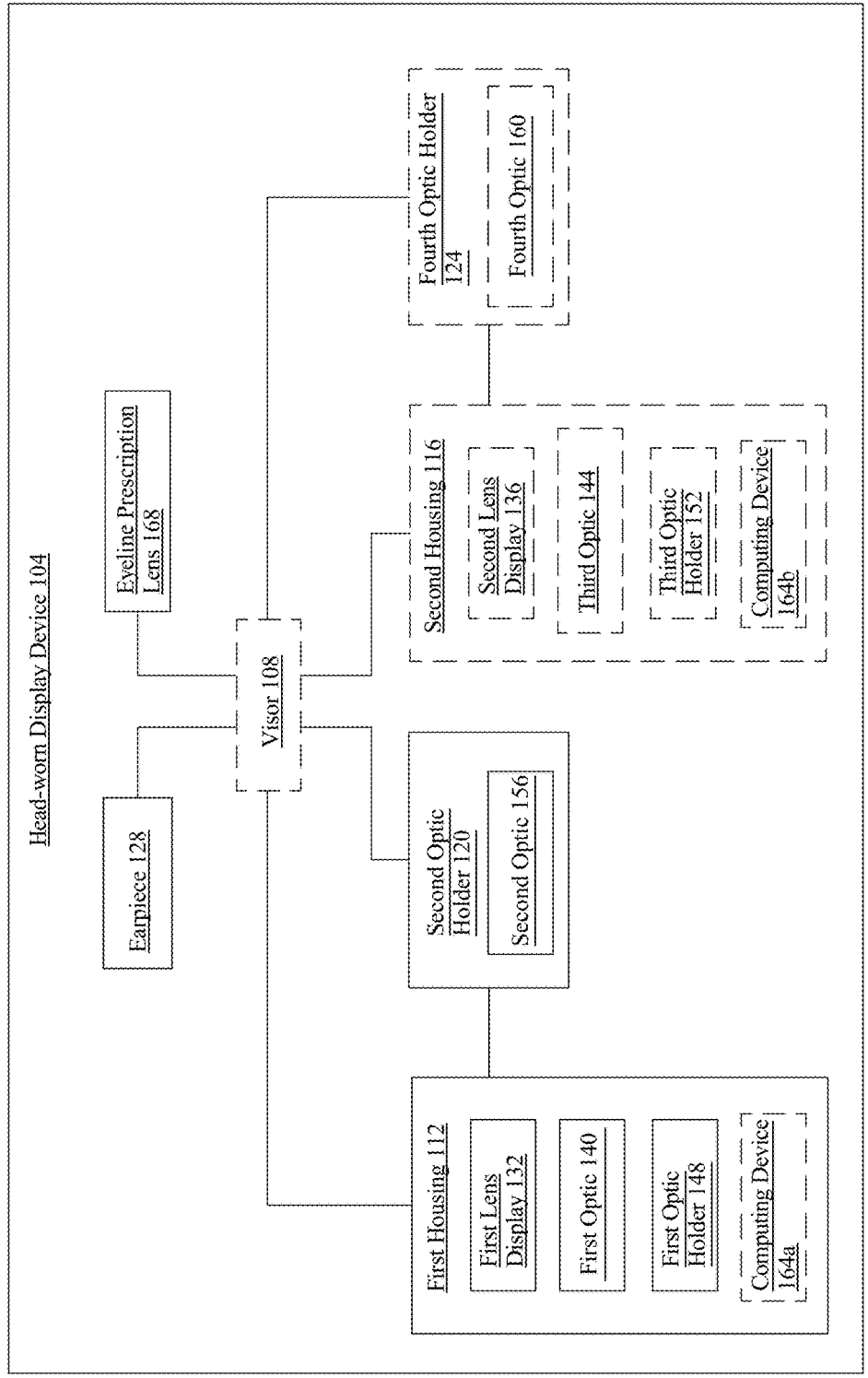
FIG. 1 is a block diagram of an exemplary lens mechanism for a head-worn display device.

Referring now to FIG. 1, a block diagram of an exemplary lens mechanism 100 for a head-worn display device 104 is illustrated. For the purposes of this disclosure, a "head-worn display device" is a display device that a user can wear on the user's head. As a non-limiting example, the head-worn display device 104 may include a headset, eyeglasses, and the like. In some embodiments, the head-worn display device 104 disclosed herein may be also referred as a "display device," "display," and the like. An exemplary configuration of the head-worn display device 104 is shown in FIG. 8-14B. For the purposes of this disclosure, a "user" is any person that uses the head-worn display device. For the purposes of this disclosure, a "display device" is a device that presents visual information or data. As a non-limiting example, the head-worn display device 104 may present visual information or data in one or more forms of text, graphics, images, video, animation, and the like. In some embodiments, the head-worn display device 104 may be configured to provide a way for the user to view and/or interact with information, including but not limited to at least an image from a camera, and/or the like. The at least an image and the camera disclosed herein is further described below. Additionally or alternatively, the head-worn display device 104 disclosed herein may be consistent with stereoscopic apparatus found in U.S. Pat. No. 11,351, 006, filed on Jun. 7, 2022, entitled "SYSTEM FOR STEREOSCOPIC VISUALIZATION ENABLING DEPTH PERCEPTION OF A SURGICAL FIELD,' the entirety of which is incorporated herein as a reference.

With continued reference to FIG. 1, in some embodiments, a head-worn display device 104 may include a visor 108. For the purposes of this disclosure, a "visor" is a front piece of a head-worn display device. In some embodiments, the visor 108 of the head-worn display device 104 may be configured to cover a user's eyes. As a non-limiting example, the head-worn display device 104 may completely cover the user's eyes. As another non-limiting example, the head-worn display device 104 may partially cover the user's eyes such that the user can see a view over the head-worn display device 104 in the user's peripheral vision. In some embodiments, the visor 108 may include various shapes, sizes, colors, and the like. As a non-limiting example, the visor 108 may be curved, flat, or indented in shape, and the like. As another non-limiting example, the visor 108 may be opaque. For the purposes of this disclosure, "opaque" refers to blocking the passage of light to an object. As another non-limiting example, the visor 108 may be transparent. For the purposes of this disclosure, "transparency" refers to allowing light to pass through an object. As another non-limiting example, the visor 108 may be partially opaque and/or partially transparent. In some embodiments, the visor 108 may be configured to protect the user from foreign factors. As a non-limiting example, the foreign factors may include dusts, debris, liquids, and the like. In some embodiments, the visor 108 may include an aperture and/or indented surface, where a first housing 112, a second housing 116, a second optic holder 120 and/or a fourth optic holder 124 may be attached to the visor 108. As a non-limiting example, the first housing 112, the second housing, the second optic holder 120 and/or the fourth optic holder 124 may be attached on the visor 108 using glue, snap-fits, screws, some combinations thereof, or any attachment methods suitable for the head-worn display device 104. The first housing 112, the second housing, the second optic holder 120 and the fourth optic holder 124 disclosed herein are further describe below. In some embodiments, the visor 108 may further include features such as latches, clips, or other fasteners that help to secure a lens mechanism 100 in place during use. In some embodiments, the visor 108 may include one or more optical markers or alignment indicators that are visible (through human eye, microscope, any other imaging system, and/or the like) and allow for accurate positioning of devices and/or components. As a non-limiting example, the visor 108 may include the optical marker that indicates a spot where the second optic holder 120 may be disposed on. As another non-limiting example, the visor 108 may include the optical marker that indicates where to hold to remove the second optic holder 120 from the visor 108. In some embodiments, the visor 108 may include one or more surface coatings and/or modifications that reduce the likelihood of unwanted adhesion or interference with the visor from external factors such as but not limited to liquid, debris, dusts, fingerprints, and the like. An exemplary configuration of the visor 108 is shown in FIGS. 8-13.

With continued reference to FIG. 1, in some embodiments, a head-worn display device 104 may include an earpiece 128. For the purposes of this disclosure, an "earpiece" is a part of a head-worn display device that supports the head-worn display device on a user's ear. In some embodiments, the head-worn display device 104 may include two earpieces 128. In some embodiments, each of the two earpieces 128 may fit around each of two ears of the user. In some embodiments, the earpieces 128 may include various shapes, sizes, colors, and the like. As a non-limiting example, the earpiece 128 may be bent down behind the ear of the user and follow the contour of a skull of the user, resting evenly against it. As another non-limiting example, the earpiece 128 may be straight and hold the spectacles on primarily by pressure against the side of the user's head. As another non-limiting example, the earpiece 128 may be curved around the ear and extend to the level of the ear lobe. In some embodiments, the nose bridge may be attached on a visor 108 of the head-worn display device 104. As a non-limiting example, the earpieces 128 may be attached on the visor 108 using glue, snap-fits, screws, some combinations thereof, or any attachment methods suitable for the head-worn display device 104. An exemplary configuration of the earpieces 128 is shown in FIG. 8-11 and FIG. 13.

Figure 8:
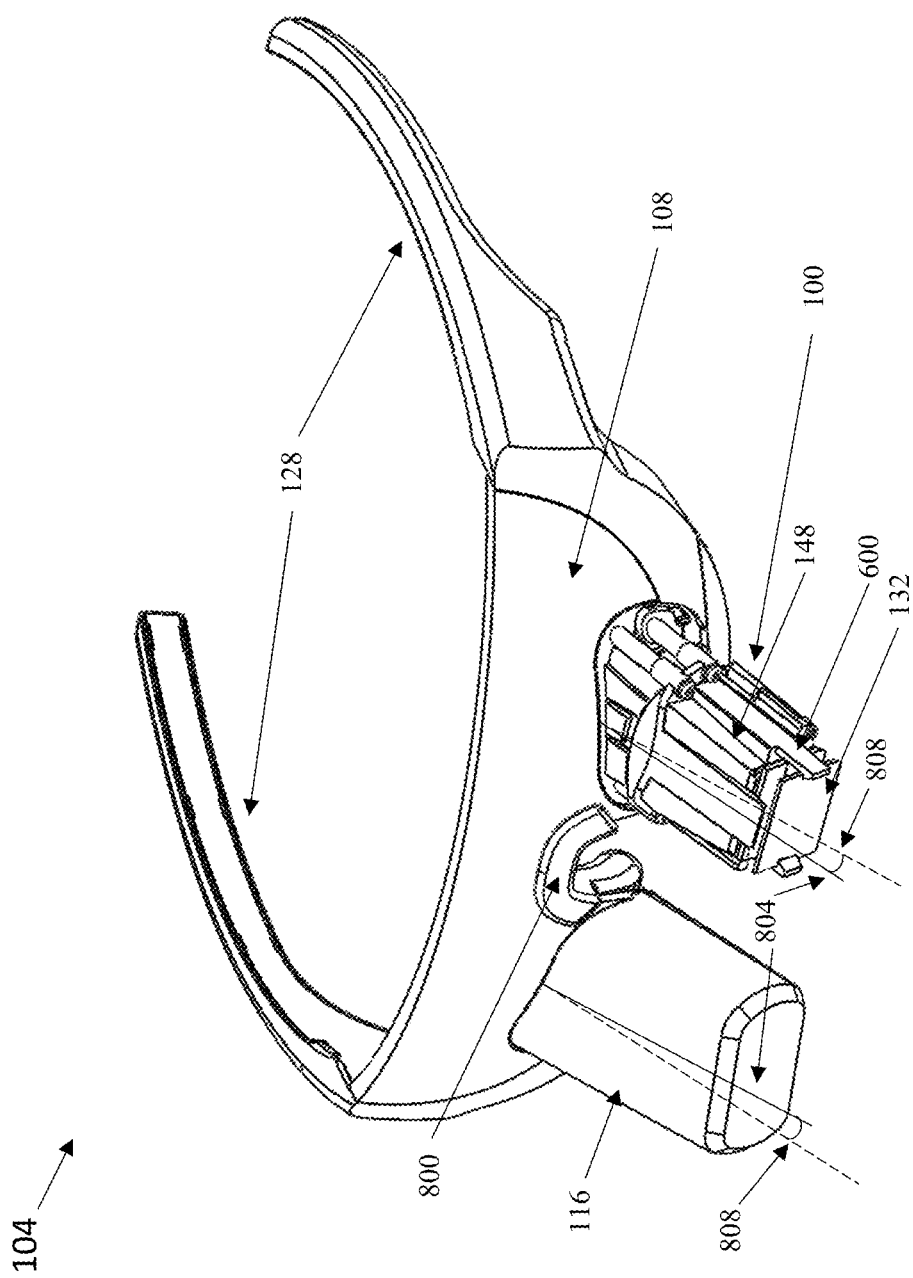
FIG. 8 is an illustration of an exemplary embodiment of a head-worn display device.
Figure 13:
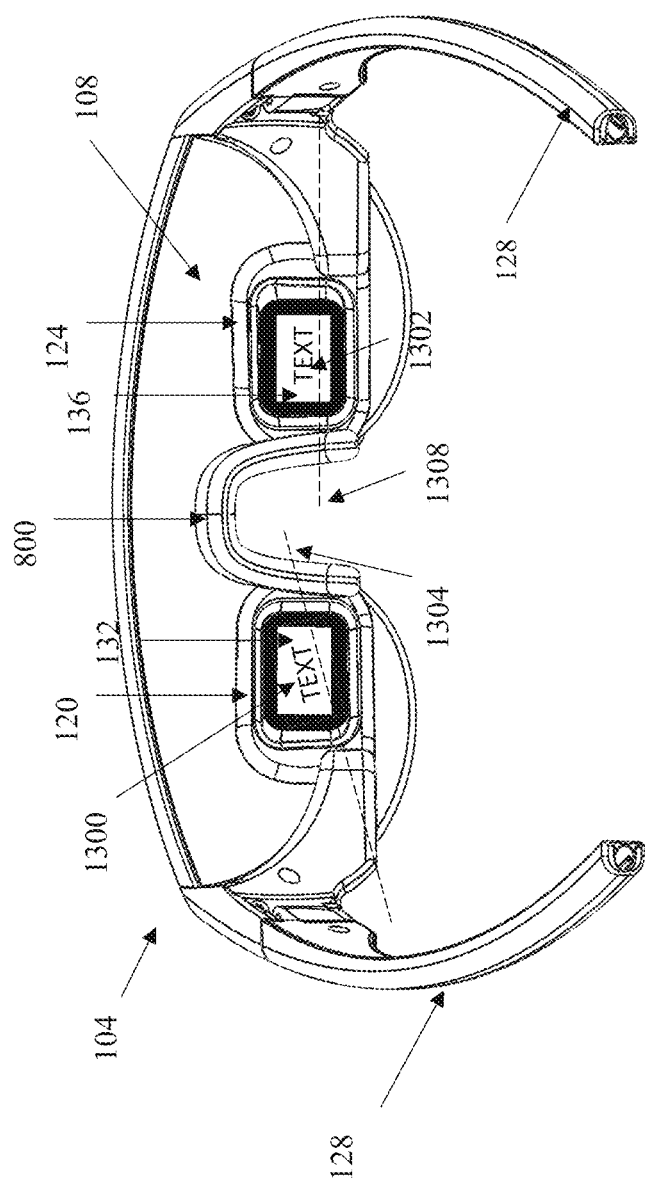
FIG. 13 is an illustration of an exemplary embodiment of a head-worn display device displaying at least an image.

With continued reference to FIG. 1, in some embodiments, a head-worn display device 104 may include a nose bridge. For the purposes of this disclosure, a "nose bridge"

is a part of a head-worn display device that rests on a user's nose. In some embodiments, the nose bridge may include various shapes, sizes, colors, and the like. In some embodiments, the nose bridge may be attached to a visor 108 of the head-worn display device 104. As a non-limiting example, the nose bridge may be attached on the visor 108 using glue, snap-fits, screws, some combinations thereof, or any attachment methods suitable for the head-worn display device 104. An exemplary configuration of the nose bridge is shown in FIG. 8 and FIG. 13. Persons skilled in the art, upon reviewing the entirety of this disclosure, may appreciate various methods for attaching earpieces 128 and the nose bridge to the visor 108 of the head-worn display device 104.

With continued reference to FIG. 1, a lens mechanism 100 for a head-worn display device 104 includes a first housing 112. For the purposes of this disclosure, a "housing" is an outer structure configured to contain a plurality of components, such as, without limitation, components of the lens mechanism 100 as described in this disclosure. In some embodiments, the lens mechanism 100 may include a plurality of housings such as but not limited to a second housing 116, where the first housing 112 is for a user's left eye and the second housing 116 is for the user's right eye or vice versa. The second housing 116 may be consistent with the first housing 112. In some cases, the housing (the first housing 112 and/or the second housing 116) may include a durable, lightweight material such as without limitation, polymer, metal, and/or the like. In some embodiments, the first housing 112 and the second housing 116 may include one or more optical markers or alignment indicators that are visible (through human eye, microscope, any other imaging system, and/or the like) and allow for accurate positioning of devices and/or components. In other non-limiting example, the first housing 112 and the second housing 116 may include one or more surface coatings and/or modifications that reduce the likelihood of unwanted adhesion or interference with external components such as, without limitation, external device as described in further detail below. Additionally, or alternatively, the first housing 112 and the second housing 116 may further include features such as latches, clips, or other fasteners that help to secure apparatus 100 in place during use. An exemplary configuration of the first housing 112 or the second housing 116 are shown in FIG. 4A-B and FIGS. 8-12.

With continued reference to FIG. 1, in an embodiment, a first housing 112 and/or a second housing 116 may be designed and configured to protect sensitive components of the lens mechanism 100 from damage or contamination. As a non-limiting example, the first housing 112 and/or the second housing 116 may protect components of the lens mechanism 100 from debris, dusts, rain, wind, external forces, and any mechanical damage thereof. In another embodiments, the first housing 112 and/or the second housing 116 may be configured to block ambient light. As a non-limiting example, the first housing 112 and/or the second housing 116 may be opaque such that the first housing 112 and/or the second housing 116 can block ambient light. An exemplary embodiment of the housing (the first housing 112 or the second housing 116) that blocks the ambient light is shown in FIG. 4B. For the purposes of this disclosure, "ambient light" is existing light surrounding a head-worn display device. As a non-limiting example, the ambient light may include natural light such as but not limited to sunlight or moonlight. As another non-limiting example, the ambient light may include light from an artificial source such as but not limited to light bulbs, lamps, and the like. As a non-limiting example, the ambient light may include any light from the light bulbs and the lamps of a surgery operating room.

Figure 9:
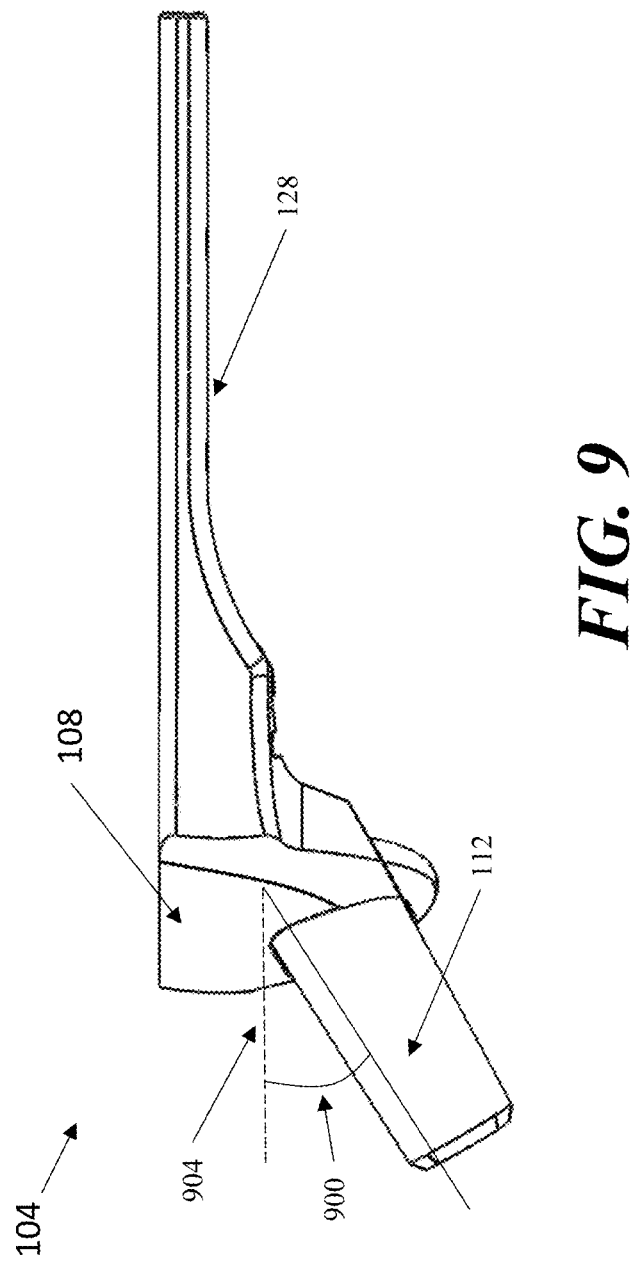
FIG. 9 is an illustration of an exemplary embodiment of a side view of a head-worn display device.

With continued reference to FIG. 1, a first housing 112 is disposed on visor 108 of a head-worn display device 104. In some embodiments, a second housing 116 may be disposed on visor 108 of the head-worn display device 104 as the first housing 112 is disposed on visor 108. As a non-limiting example, the first housing 112 and the second housing 116 may be disposed on the visor 108 using glue, snap-fits, screws, some combinations thereof, or any attachment methods suitable for the head-worn display device 104. As another non-limiting example, the first housing 112 and the second housing 116 may be disposed in an aperture or an indented surface of the visor 108. In some embodiments, the first housing 112 and the second housing 116 may be angularly disposed with respect to the visor 108 of the head-worn display device 104 at a downward angle relative to a horizon plan of the visor 108 as shown in FIG. 9. As a non-limiting example, when a user, such as but not limited to a surgeon, is operating a surgery, the user may only need to look down to watch at least an image from a camera, where the at least an image and the camera are disclosed below. In some embodiments, the first housing 112 and the second housing 116 may be angularly disposed relative to one another along a vertical plane of the visor 108 of the head-worn display device 104 by an accommodation angle as shown in FIG. 8. For the purposes of this disclosure, an "accommodation angle" is an angle between a first housing and a second housing. As a non-limiting example, the accommodation angle may include from zero degrees, meaning the first housing 112 and the second housing 116 can be parallel to each other, to forty-five degrees, and the like. Additional disclosure related to disposing the first housing 112 and/or the second housing 116 on the visor 108 may utilize a mechanism found in U.S. Pat. No. 9,247,866, filed on Feb. 2, 2016, entitled "ROTATIONAL STABILIZING LOCKING MECHANISM," the entirety of which is incorporated as a reference.

With continued reference to FIG. 1, a first housing 112 includes a first lens display 132. In some embodiments, a second housing 116 may include a second lens display 136. The second lens display 136 may be consistent with the first lens display 132. For the purposes of this disclosure, a "lens display" is a display device that is configured is configured to emit light waves to display at least an image. For the purposes of this disclosure, "light wave" is electromagnetic radiation that can be perceived by a user's eye. The lens display may be consistent with any display device disclosed in the entirety of this disclosure. In some embodiments, the first lens display 132 and the second lens display 136 may include different technologies, such as liquid crystal display (LCD), a light-emitting diode (LED), organic light-emitting diode (OLED), plasma, projection, touch screen, and/or the like. In some embodiments, the first lens display 132 and the second lens display 136 may include varying resolutions, sizes, and aspect ratios. Persons skilled in the arts, upon reviewing the entirety of this disclosure, may appreciate various lens displays that may be used for a lens mechanism 100.

With continued reference to FIG. 1, in some embodiments, a first lens display 132 and/or a second lens display 136 may receive at least an image from a camera. As a non-limiting example, the first lens display 132 may receive and/or display a first image of the at least an image from a first camera. As another non-limiting example, the second lens display 136 may receive and/or display a second image of the at least an image from a second camera. In some embodiments, the first camera and the second camera may be configured for stereoscopic vision. As a non-limiting example, the second image of the second lens display 136 and the first image of the first lens display 132 may be different such that the first lens display 132 and the second lens display 136 may display stereoscopic vision. In an embodiment, the second image of the second lens display 136 may be equivalent to the first image of the first lens display 132. As used in this disclosure, a "camera" is a device that is configured to sense electromagnetic radiation and generate an image representing the electromagnetic radiation. As a non-limiting example, the electromagnetic radiation may include visible light, infrared, ultraviolet, radio waves, microwaves, x-rays, gamma rays, and the like. In some embodiments, the camera may be an external device. As a non-limiting example, the camera may include an external separate device to generate the at least an image. As used in this disclosure, an "image" is information representing at least a physical scene, space, and/or object. As a non-limiting example, the at least an image may include a human body, any organs in the human body, a surgeon's (user's) hand, surgical tools, operation room, surgical machines, any biological and/or chemical substances, and the like. In some cases, the at least an image may be generated by the camera. The at least an image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively where "image" is used as a verb, in this disclosure, it refers to generation and/or formation of an image. Additional disclosure related to the at least an image and the camera may be found in U.S. patent application Ser. No. 18/129,601, filed on Mar. 31, 2023, entitled "FLEXIBLE AND TENSIONED CAMERA APPARATUS WITH ELECTRONIC MODULE SYSTEM FOR ENABLING MANEUVERABLE STEREOCSCOPIC FILED OF VIEW," and U.S. patent application Ser. No. 18/129,678, filed on Mar. 31, 2023, entitled "STEREOCSCOPIC CAMERA ADAPTER FOR ENABLING DOWN-HOLE DATA CAPTURE AND TRANSMISSION," the entirety of which are incorporated as references.

With continued reference to FIG. 1, in some embodiments, a camera may include one or more optics. Exemplary non-limiting optics include spherical lenses, aspherical lenses, reflectors, polarizers, filters, windows, aperture stops, and the like. In some cases, the camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, the camera may be sensitive within a non-visible range of electromagnetic radiation, such as without limitation infrared.

With continued reference to FIG. 1, an exemplary camera may include an OpenMV Cam H7 from OpenMV, LLC of Atlanta, Ga., U.S.A. OpenMV Cam includes a small, low power, microcontroller which allows execution of processes. OpenMV Cam comprises an ARM Cortex M7 processor and a 640×480 image sensor operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detect motion, for example by way of frame differencing algorithms; detect markers, for example blob detection; detect objects, for example face detection; track eyes; detection persons, for example by way of a trained machine learning model; detect camera motion, for example by way of optical flow detection; detect and decode barcodes; capture images; and record video. Persons skilled in the art, upon reviewing the entirety of this disclosure, will be aware of various types of cameras that may be used for the disclosure.

With continued reference to FIG. 1, in some embodiments, a camera may include a plurality of cameras, where the plurality of cameras may capture two or more perspectives for use in three-dimensional display. The camera may include a stereo-camera. As used in this disclosure, a "stereo-camera" is a camera that senses two or more images from two or more vantages. As used in this disclosure, a "vantage" is a location of a camera relative a scene, space and/or object which the camera is configured to sense. In some cases, a stereo-camera may determine depth of an object in a scene as a function of parallax. As used in this disclosure, "parallax" is a difference in perceived location of a corresponding object in two or more images. An exemplary stereo-camera is TaraXL from e-con Systems, Inc of San Jose, Calif. TaraXL is a USB 3.0 stereo-camera which is optimized for NVIDIA® Jetson AGX Xavier™/Jetson™ TX2 and NVIDIA GPU Cards. TaraXL's accelerated Software Development Kit (TaraXL SDK) is capable of doing high quality 3D depth mapping of WVGA at a rate of up to 60 frames per second. TaraXL is based on MT9V024 stereo sensor from ON Semiconductor. Additionally, TaraXL includes a global shutter, houses 6 inertial measurement units (IMUs), and allows mounting of optics by way of an S-mount lens holder. TaraXL may operate at depth ranges of about 50 cm to about 300 cm.

With continued reference to FIG. 1, a first housing 112 includes a first optic 140. In some embodiments, a second housing 116 may include a third optic 144. The third optic 144 may be consistent with the first optic 140. In some embodiments, third optic 144 may include a magnifying lens. For the purposes of this disclosure, a "magnifying lens" is a lens that is configured to magnify at least an image of a lens display. In some embodiments, the first optic 140 may be configured to magnify the at least an image of a first lens display 132. In some embodiments, the third optic 144 may be configured to magnify the at least an image of a second lens display 136. As a non-limiting example, the first lens display 132 and the second lens display 136 may emit light waves to display the at least an image such as but not limited to a first image and a second image, then each of the first optic 140 and the third optic 144 may refract the light waves, meaning magnifying the first image and the second image. exemplary embodiment of a mechanism of the first optic 140 and/or the third optic 144 is shown in FIG. 2-4B and FIG. 6.

With continued reference to FIG. 1, a first housing 112 includes a first optic holder 148. In some embodiments, a second housing 116 may include a third optic holder 152. The third optic holder 152 may be consistent with the first optic holder 148. For the purposes of this disclosure, a "relief frame" is a structure that is configured to rigidly maintain a first lens display and a first optic at a relief height. For the purposes of this disclosure, a "relief height" a distance between a lens display and a magnifying lens. In an embodiment, the relief height (Rh) may be equivalent to a focal length of the magnifying lens (the first optic 140 or the third optic 144), which may allow a surface of the lens display (the first lens display 132 or the second lens display 136) to be in focus without a prescription lens (a second optic 156 or a fourth optic 160) to a user with 20/20 vision. In some embodiments, fourth optic 160 may be consistent with third optic 144 as described above. In some embodiments, For the purposes of this disclosure, a user with "20/20 vision" refers that the user can see clearly at 20 feet what should normally be seen at that distance. For the purposes of this disclosure, a "focal length" is a distance from a magnifying lens to a focal point, where the "focal point" is a point at which light waves meet after refraction. In some embodiments, the first optic holder 148 and/or the third optic holder 152 may include a durable, lightweight material such as without limitation, polymer, metal, and/or the like. In some embodiments, the first optic holder 148 and/or the third optic holder 152 may include one or more optical markers or alignment indicators that are visible (through human eye, microscope, any other imaging system, and/or the like) and allow for accurate positioning of devices and/or components such as but not limited to the lens displays (the first lens display 132 and/or the second lens display 136), a computing device 164*a-b*, the magnifying lens (the first optic 140 and/or the third optic 144) and/or a visor 108.

Figure 5:
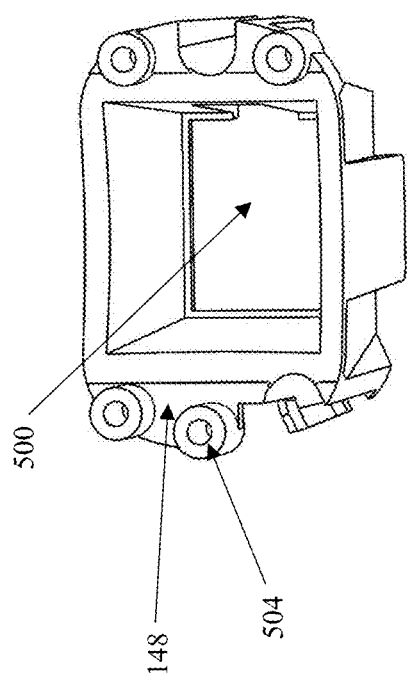
FIG. 5 is an illustration of an exemplary embodiment of a relief frame.

With continued reference to FIG. 1, a first optic holder 148 includes an aperture running through its length to allow light waves to pass from a first lens display 132 to a first optic 140. In some embodiments, a third optic holder 152 may include the aperture running through its length to allow the light waves to pass from a second lens display 136 to a third optic 144. The aperture of the third optic holder 152 may be consistent with the aperture of the first optic holder 148. In some embodiments, the first optic holder 148 and/or the third optic holder 152 may be disposed on a visor 108 of a head-worn display device 104. In an embodiment, the first optic holder 148 and/or the third optic holder 152 may include screw holes for attachment to the visor 108 of the head-worn display device 104. In another embodiment, the first optic holder 148 and/or the third optic holder 152 may include a fixture for attachment to the visor 108 of the head-worn display device 104, where the fixture is further described in detail below. An exemplary configuration of the aperture and the screw holes of the relief frame (the first optic holder 148 or the third optic holder 152) is shown in FIG. 5.

Figure 6:
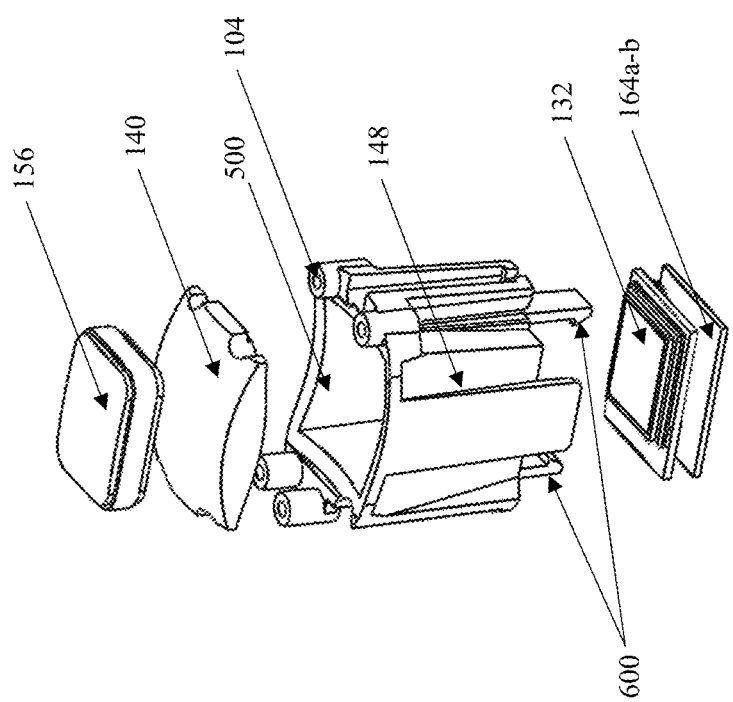
FIG. 6 is an illustration of an exemplary embodiment of an exploded view of a lens mechanism.

With continued reference to FIG. 1, in some embodiments, a first optic holder 148 and/or a third optic holder 152 may include a fixture that rigidly maintain lens displays (a first lens display 132 or a second lens display 136), or the lens displays and a computing devices 164*a-b* relative to the first optic holder 148 and/or the third optic holder 152. The computing device 164*a-b* disclosed herein is further described below. For the purposes of this disclosure, a "fixture" is a structure or a component that connects one or more elements of a head-worn display device. In an embodiment, the fixture may be permanent. In another embodiment, the fixture may be temporary, where the one or more elements of the head-worn display device 104 can be disassembled. As a non-limiting example, the fixture may include a pint joint, prismatic joint, ball joint, knuckle joint, turnbuckle, cotter pin, bolted joint, snap-fits, and the like. For the purposes of the disclosure, a "snap-fit" is an assembly method used to attach parts to form a final product by pushing the parts' interlocking components together. An exemplary configuration of the snap-fit of the fixture used in the relief frame (the first optic holder 148 and/or the third optic holder 152) is shown in FIG. 6 and FIG. 8. As another non-limiting example, the fixture may include rigid coupling, such as beam coupling, bellows coupling, bushed pin coupling, constant velocity, split-muff coupling, diaphragm coupling, disc coupling, donut coupling, elastic coupling, flexible coupling, fluid coupling, gear coupling, grid coupling, Hirth joints, hydrodynamic coupling, jaw coupling, magnetic coupling, Oldham coupling, sleeve coupling, tapered shaft lock, twin spring coupling, rag joint coupling, universal joints, or any combination thereof. As another non-limiting example, the fixture may include soldering, welding, and the like. In some embodiments, the fixture may connect the lens display (the first lens display 132 or the second lens display 136) to the relief frame (the first optic holder 148 or the third optic holder 152), the computing device 164*a-b* to the relief frame (the first optic holder 148 or the third optic holder 152), the relief frame (the first optic holder 148 or the third optic holder 152) to the visor 108, the prescription lens holder (the second optic holder 120 or the fourth optic holder 124) to the visor 108, and the like. The second optic holder 120 and the fourth optic holder 124 disclosed herein are described further in detail below.

With continued reference to FIG. 1, head worn display device 104 may include a computing device 164*a-b*. Computing device 164*a-b* may include a processor. Processor may include, without limitation, any processor described in this disclosure. Processor may be included in a computing device. Computing device 164*a-b* may include any computing device as described in this disclosure, including without limitation a microcontroller, microprocessor, digital signal processor (DSP) and/or system on a chip (SoC) as described in this disclosure. Computing device 164*a-b* may include, be included in, and/or communicate with a mobile device such as a mobile telephone or smartphone. Computing device 164*a-b* may include a single computing device operating independently, or may include two or more computing device operating in concert, in parallel, sequentially or the like; two or more computing devices may be included together in a single computing device or in two or more computing devices. Computing device 164*a-b* may interface or communicate with one or more additional devices as described below in further detail via a network interface device. Network interface device may be utilized for connecting Computing device 164*a-b* to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 164*a-b* may include but is not limited to, for example, a computing device or cluster of computing devices in a first location and a second computing device or cluster of computing devices in a second location. Computing device 164*a-b* may include one or more computing devices dedicated to data storage, security, distribution of traffic for load balancing, and the like. Computing device 164*a-b* may distribute one or more computing tasks as described below across a plurality of computing devices of computing device, which may operate in parallel, in series, redundantly, or in any other manner used for distribution of tasks or memory between computing devices. Computing device 164*a-b* may be implemented, as a non-limiting example, using a "shared nothing" architecture.

With continued reference to FIG. 1, Computing device 164*a-b* may be designed and/or configured to perform any method, method step, or sequence of method steps in any embodiment described in this disclosure, in any order and with any degree of repetition. For instance, Computing device 164*a-b* may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 164*a-b* may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, in some embodiments, a first housing 112 and/or a second housing 116 may include a computing device 164*a-b*. In some embodiments, computing device 164*a-b* of first housing 112 and/or second housing 116 may include a display daughter board. As a non-limiting example, the computing device 164*a-b* may include a daughter board, display daughter board, and the like. For the purposes of this disclosure, a "daughter board" is a circuit board that plugs into and extends a circuitry of another circuit board. For the purposes of this disclosure, a "display daughter board" is a circuit board that plugs into and extends a circuitry of a lens display. In some embodiments, the display daughter board may be configured to enhance functions of the lens display (a first lens display 132 and/or a second lens display 136) or provides the lens displays (the first lens display 132 and/or the second lens display 136) with new functions. As a non-limiting example, the display daughter board and/or computing device 164*a-b* may include electronics to further support the lens display (the first lens display 132 and/or the second lens display 136) functions such as signal input conversion, clocking, hardware drivers, software drivers, or independent functions such as an accelerometer, gyroscope, microphone, or speaker, or some combination thereof. For the purposes of this disclosure, a "speaker" is a device that converts electrical signals into sound waves that can be heard by the human ear. For the purposes of this disclosure, a "microphone" is a device that converts sound waves into electrical signals. The microphone may be a type of transducer that is used to capture audio signals and convert them into an electrical form that can be amplified, recorded, or transmitted to other devices. In some embodiments, the first optic holder 148 may be configured to rigidly maintain the display daughter board and/or computing device 164*a*. In some embodiments, the third optic holder 152 may be configured to rigidly maintain the computing device 164*b*.

With continued reference to FIG. 1, a computing device may include a memory communicatively connected to at least a processor. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, in some embodiments, a head-worn display device 104 may include one or more elements of dedicated signal processing hardware and/or software modules. This may include filters, filter banks including analysis and synthesis banks, fast Fourier Transform (FFT) calculation modules, signal generators, matrix operation calculators, or the like. In some embodiments, the head-worn display device 104 may be configured to perform one or more signal processing steps on a signal, where the signal is any signal disclosed in the entirety of this disclosure. As used in this disclosure, a "signal" is any intelligible representation of data, for example from one device to another. A signal may include an optical signal, a hydraulic signal, a pneumatic signal, a mechanical, signal, an electric signal, a digital signal, an analog signal and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

With continued reference to FIG. 1, as a non-limiting example, a head-worn display device 104 may analyze, modify, and/or synthesize a signal representative of characteristic. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which varying continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. In some embodiments, a filter bank may be used, such as but not limited to analysis banks, synthesis banks, FFT filter banks, and the like. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, a lens mechanism 100 of a head-worn display device 104 includes a second optic holder 120. In some embodiments, the lens mechanism 100 of the head-worn display device 104 may include a fourth optic holder 124. The fourth optic holder 124 may be consistent with the second optic holder 120. For the purposes of this disclosure, a "prescription lens holder" is a structure configured to hold a prescription lens. The prescription lens disclosed herein is further described below. In some embodiments, the second optic holder 120 and/or the fourth optic holder 124 may include a durable, lightweight material such as without limitation, polymer, metal, and/or the like. In some embodiments, the second optic holder 120 and/or the fourth optic holder 124 may include one or more optical markers or alignment indicators that are visible (through human eye, microscope, any other imaging system, and/or the like) and allow for accurate positioning of devices and/or components such as but not limited to prescription lens (a second optic 156 and a fourth optic 160) and/or a visor 108. In some embodiments, the second optic holder 120 and/or the fourth optic holder 124 may further include features such as fixtures, latches, clips, or other fasteners that help to secure the prescription lens holders and/or the prescription lens in place. An exemplary configuration of the prescription lens holder (the second optic holder 120 and the fourth optic holder 124) is shown in FIGS. 2, 7, 10, 12 and 13.

With continued reference to FIG. 1, a second optic holder 120 includes a second optic 156. In some embodiments, a fourth optic holder 124 may include a fourth optic 160. The fourth optic 160 may be consistent with the second optic 156. For the purposes of this disclosure, a "prescription lens" is a lens that is configured to correct refractive errors of a user's eye and improve a vision of the user's eye. As a non-limiting example, the refractive errors of the user's eye may include myopia, hypermetropia, astigmatism, presbyopia, and the like. An exemplary configuration of the second optic 156 and/or the fourth optic 160 is shown in FIG. 2-4B, FIG. 6-7 and FIG, 10-12.

With continued reference to FIG. 1, in some embodiments, a second optic 156 and/or a fourth optic 160 may include various types, profiles, thickness, corrective prescriptions, and the like. As a non-limiting example, the second optic 156 and/or the fourth optic 160 may include a single vision lens, bifocal lens, trifocal lens, plano lens, and the like. As another non-limiting example, the second optic 156 and/or the fourth optic 160 may include biconvex lens, plano-convex lens, convex-concave lens, meniscus lens, plano-concave lens, biconcave lens, and the like. For the purposes of this disclosure, a "corrective prescription" is an order that specifies values of parameters to construct and/or dispense a prescription lens for a user based on eye examinations. As a non-limiting example, the corrective prescription may include power of the prescription lens, pupillary distance, prism, and the like. For the purposes of this disclosure, an "eye examination" is a test or an examination pertaining to eyes. As a non-limiting example the eye examination may include a series of tests performed to assess vision and ability to focus on and discern objects. As another non-limiting example, the eye examination may include an external examination, followed by specific tests for visual acuity, pupil function, extraocular muscle motility, visual fields, intraocular pressure and ophthalmoscopy through a dilated pupil. As another non-limiting example, the eye examination may include visual acuity, refraction, ocular motility, and the like. In an embodiment, the second optic 156 and the fourth optic 160 may include equivalent types, profiles and/or corrective prescription of the prescription lens. In another embodiment, the second optic 156 and the fourth optic 160 may include different correction types, profiles and/or corrective prescription of the prescription lens.

With continued reference to FIG. 1, in some embodiments, a second optic 156 is interchangeable. In some embodiments, a fourth optic 160 may be interchangeable. For the purposes of this disclosure, "interchangeability" is a capability of replacing or changing places with another component. As a non-limiting example, the second optic 156 may be interchanged with another prescription lens with different correction prescription. In some embodiments, the second optic 156 is located over a first optic 140 (as shown in FIGS. 2-4B and FIG. 6). In some embodiments, the fourth optic 160 may be located over a third optic 144 (as shown in FIGS. 2-4B and FIG. 6).

Figure 7:
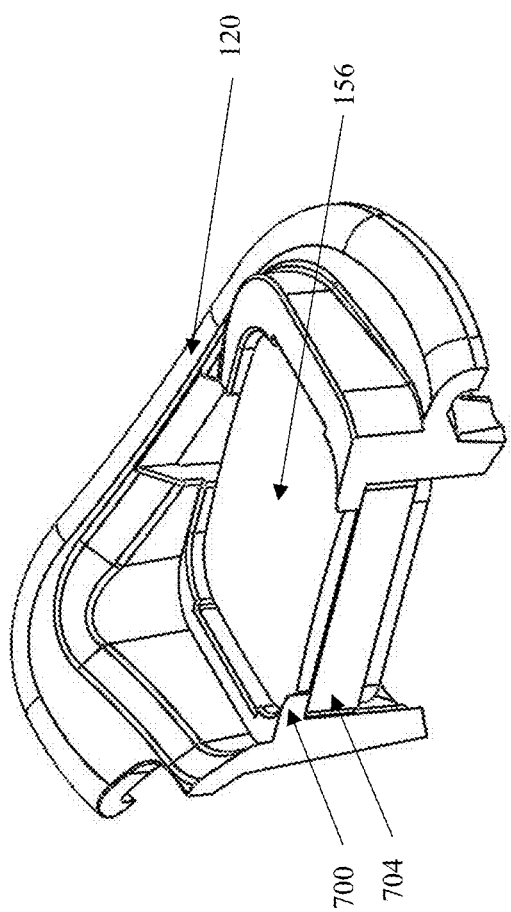
FIG. 7 is an illustration of an exemplary embodiment of a prescription housed in a prescription lens holder.

With continued reference to FIG. 1, in some embodiments, a second optic 156 and/or a fourth optic 160 may include a protrusion, where the second optic 156 and/or the fourth optic 160 can be temporary disposed in a second optic holder 120 and/or a fourth optic holder 124. For the purposes of this disclosure, a "protrusion" is a structure that is protruded from a surface. An exemplary configuration of the protrusion of the second optic 156 and/or the fourth optic 160 is shown in FIG. 7. In some embodiments, the second optic 156 and/or a fourth optic 160 may include any fixtures, screw holes, or any other components that can dispose the second optic 156 and/or a fourth optic 160 to the second optic holder 120 and/or the fourth optic holder 124. In some embodiments, the second optic 156 and/or a fourth optic 160 may be rigidly held relative to one another on top by friction contact between a ledge of the second optic holder 120 and/or the fourth optic holder 124 and the protrusion of the second optic 156 and/or a fourth optic 160 and by contact with a first optic 140 and/or a third optic 144 from the bottom. For the purposes of this disclosure, a "ledge" is a narrow horizontal surface projecting from a surface. An exemplary configuration of the ledge of the second optic 156 and/or a fourth optic 160 is illustrated in FIG. 7. In some embodiments, the second optic holder 120 and/or the fourth optic holder 124 may include a magnetic or mechanical attachment mechanism that can securely hold the second optic 156 and/or a fourth optic 160 in place. In some embodiments, the second optic holder 120 and/or the fourth optic holder 124 may include a locking mechanism that can be released from the visor 108 using a button, lever, and the like.

Figure 10:
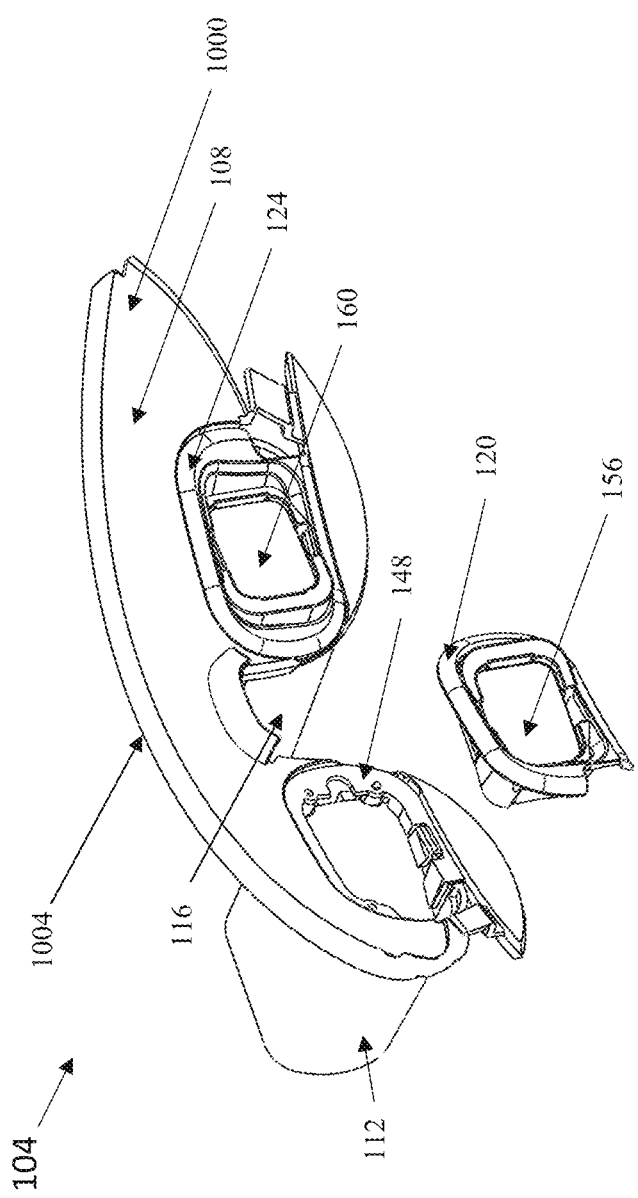
FIG. 10 is an illustration of an exemplary embodiment of a head-worn display device with prescription lens holders of a lens mechanism.

With continued reference to FIG. 1, a second optic holder 120 and/or a fourth optic holder 124 may be configured to be disposed on a visor 108 of a head-worn display device 104. In some embodiments, the second optic holder 120 and/or the fourth optic holder 124 may be configured to be removably disposed in the visor 108 of the head-worn display device 104. For the purposes of this disclosure, "removably disposed" refers an ability for a structure to be removed and added to another structure. In some embodiments, the second optic holder 120 is configured to removably dispose the second optic 156 to the visor 108 of the head-worn display device 104. In some embodiments, the fourth optic holder 124 may be configured to removably dispose the fourth optic 160 to the visor 108 of the head-worn display device 104. The capability to be removably disposed in the visor 108 may allow a user to interchange the second optic holder 120 and/or the fourth optic holder 124 to another prescription lenses. In some embodiments, each of the second optic holder 120 and/or the fourth optic holder 124 may be configured to removably dispose the second optic 156 and/or the fourth optic 160 to a first optic holder 148 and a third optic holder 152. As an exemplary configuration, FIG. 10 illustrates the capability of second optic holder 120 and/or the fourth optic holder 124 to be removably disposed in the first optic holder 148 and the third optic holder 152. As a non-limiting example, the second optic holder 120 and/or the fourth optic holder 124 may be removably disposed in another components, such as but not limited to the visor 108 and/or the relief frame, using screws, fixtures, or any other components thereof suitable for a lens mechanism 100 of the head-worn display device 104.

Figure 11:
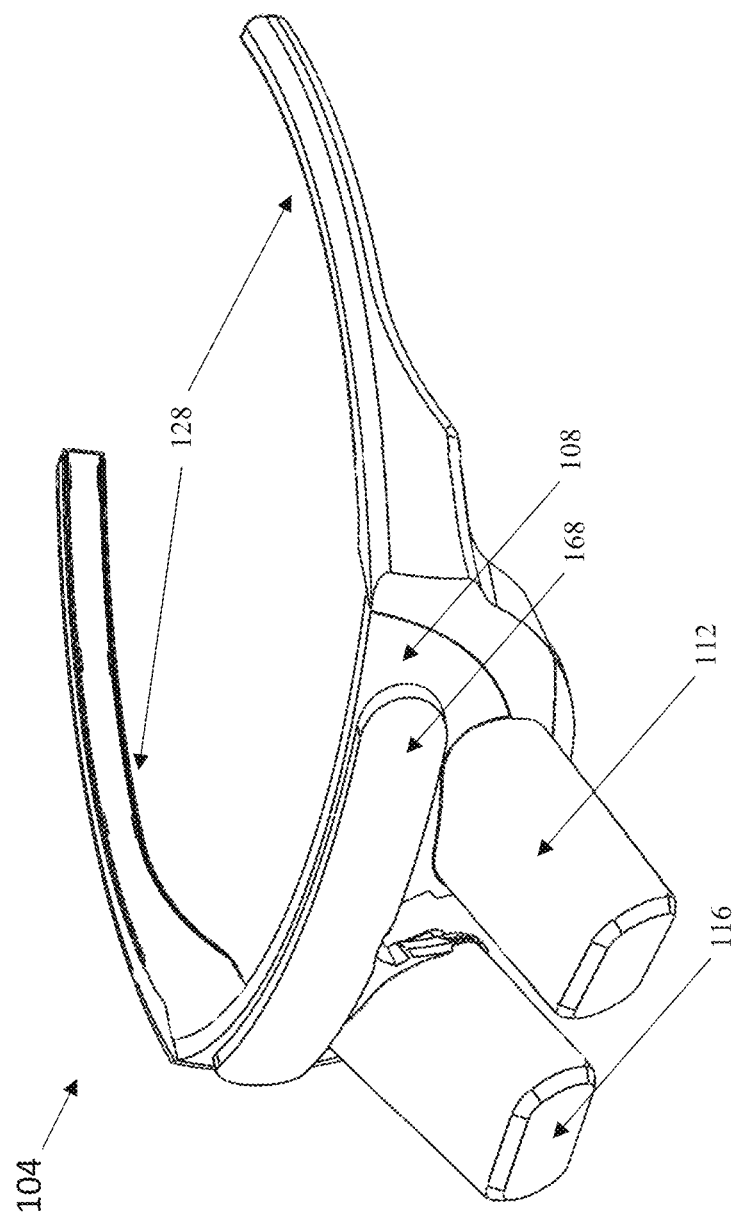
FIG. 11 is an illustration of an exemplary embodiment of a head-worn display device with an eye-line prescription lens of a lens mechanism.
Figure 12:
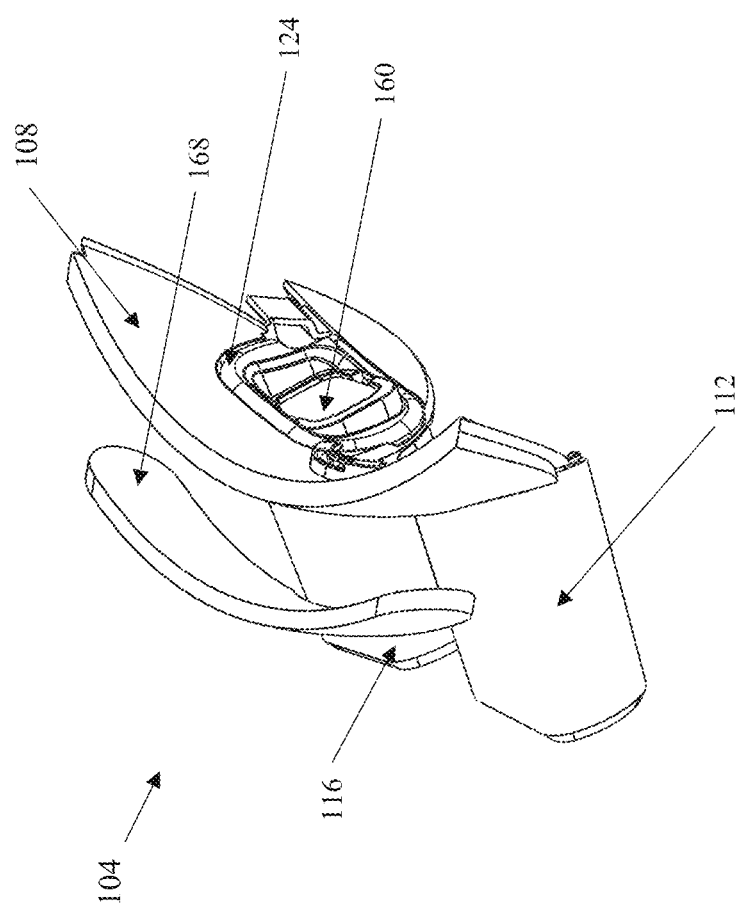
FIG. 12 is an illustration of an exemplary embodiment of an exploded view of an eye-line prescription lens of a lens mechanism on a head-worn display device.

With continued reference to FIG. 1, in some embodiments, a lens mechanism 100 may further include an eye-line prescription lens 168. For the purposes of this disclosure, an "eye-line prescription lens" is a prescription lens that is disposed along a horizontal plane of a head-worn display device. In some embodiments, the eye-line prescription lens 168 may be consistent with a second optic 156 and/or a fourth optic 160. In some embodiments, the eye-line prescription lens 168 may be configured to provide additional corrective vision when the user is looking through a horizon plane of a visor 108 of a head-worn display device 104. In some embodiments, the eye-line prescription lens 168 may include a third lens display, where the third lens display may be consistent with a first lens display 132 and/or a second lens display 136 described above. In some embodiments, the eye-line prescription lens 168 may include a computing device 164a-b and/or display daughter board, where the computing device 164a-b is described further in detail above. In some embodiments, the eye-line prescription lens 168 may include a third magnifying lens, where the third magnifying lens may be consistent with a first optic 140 and/or a third optic 144 described above. In some embodiments, the eye-line prescription lens 168 may include a third relief frame, where the third relief frame may be consistent with a first optic holder 148 and/or a third optic holder 152 described above. In some embodiments, the eye-line prescription lens 168 may include a third prescription lens holder that may be configured to rigidly hold the eye-line prescription lens 168, where the third prescription lens holder may be consistent with a second optic holder 120 and/or a fourth optic holder 124 described above. In some embodiments, the eye-line prescription lens 168 held in the third prescription lens holder may be removably disposed in the visor 108 of the head-worn display device 104. An exemplary configuration of the eye-line prescription lens 168 is illustrated in FIGS. 11-12.

Figure 2:
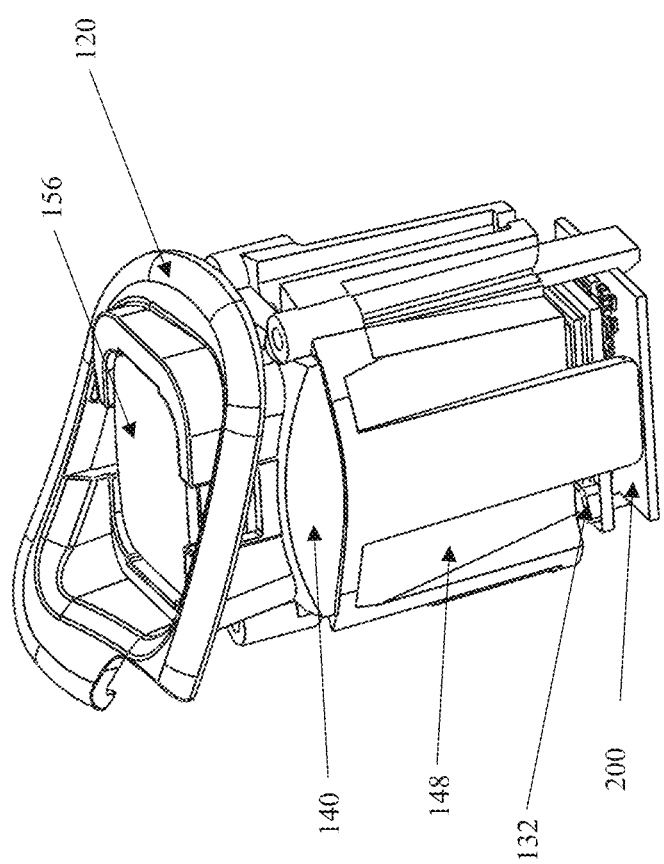
FIG. 2 is an illustration of an exemplary embodiment of a lens mechanism.

Referring now to FIG. 2, an exemplary embodiment of a lens mechanism 100 is illustrated. In some embodiments, the lens mechanism 100 may focus a view of a nearby display based on corrective prescriptions and can be interchanged with other prescription lenses. In some embodiments, the lens mechanism 100 may include two sets of relief frames (a first optic holder 148 and a third optic holder 152), lens displays (a first lens display 132 and a second lens display 136), display daughter boards 200, magnifying lenses (a first optic 140 and a third optic 144), prescription lenses (a second optic 156 and a fourth optic 160) and prescription lens holders (a second optic holder 120 and a fourth optic holder 124). In some embodiments, the magnifying lenses (the first optic 140 and the third optic 144) can be spherical, aspherical, symmetric, or asymmetric. In some embodiments, the magnifying lenses (the first optic 140 and the third optic 144) may magnify at least an image from the lens displays (the first lens display 132 and the second lens display 136) which may be located proximal to an eye of a user so that the at least an image can be resolved by the eye with 20/20 vision. In some embodiments, the lens displays (the first lens display 132 and the second lens display 136) can be connected to the display daughter boards 200 that may include electronics to further support the lens display (the first lens display 132 and/or the second lens display 136) functions such as signal input conversion, clocking, hardware drivers, software drivers, or independent functions such as an accelerometer, gyroscope, microphone, or speaker, or some combination thereof.

Referring now to FIG. 3, an exemplary embodiment of a side view of a portion of a lens mechanism 100 is illustrated. In some embodiments, a lens display (a first lens display 132 and/or a second lens display 136) and a display daughter board 200 may be positioned at a relief height (Rh) 300 from a magnifying lens (a first optic 140 and/or a third optic 144) and prescription lens (a second optic 156 and/or a fourth optic 160), maintained in position by prescription lens holders (a second optic holder 120 and a fourth optic holder 124), such that light waves 304 pass from the lens display (the first lens display 132 and/or the second lens display 136) may be bent when passing through the magnifying lens (the first optic 140 and/or the third optic 144), enabling magnification of at least an image of the lens display (the first lens display 132 and/or the second lens display 136) and correction for vision conditions to accommodate varying eye conditions such as astigmatism, myopia, hyperopia, and others. If a user's left and right eye have different correction prescriptions, unique prescription lenses can be used for the second optic 156 and the fourth optic 160. In some embodiments, the magnifying lens (the first optic 140 and/or the third optic 144) may be physically separated from the lens display (the first lens display 132 and/or the second lens display 136) by the relief frames (the first optic holder 148 and the third optic holder 152), which may maintain a fixed distance between the magnifying lens (the first optic 140 and/or the third optic 144) and the lens display (the first lens display 132 and/or the second lens display 136) called a relief height (Rh) 300. In some embodiments, the Rh 300 may be equivalent to a focal length of the magnifying lens (the first optic 140 and/or the third optic 144), which allows a surface of the lens display (the first lens display 132 and/or the second lens display 136) to be in focus without an additional prescription lens (the second optic 156 and/or the fourth optic 160) to a user with 20/20 vision. In some embodiments, the relief frames (the first optic holder 148 and/or the third optic holder 152) may include an aperture running through its length to allow light to pass from the lens displays (the first lens display 132 and/or the second lens display 136) to the magnifying lens (the first optic 140 and/or the third optic 144). The relief frame (the first optic holder 148 and/or the third optic holder 152) may further include screw holes for attachment to a visor 108. In some embodiments, in FIG. 3 the light waves 304 getting bent by the magnifying lens and the prescription lens is shown.

Figure 4A:
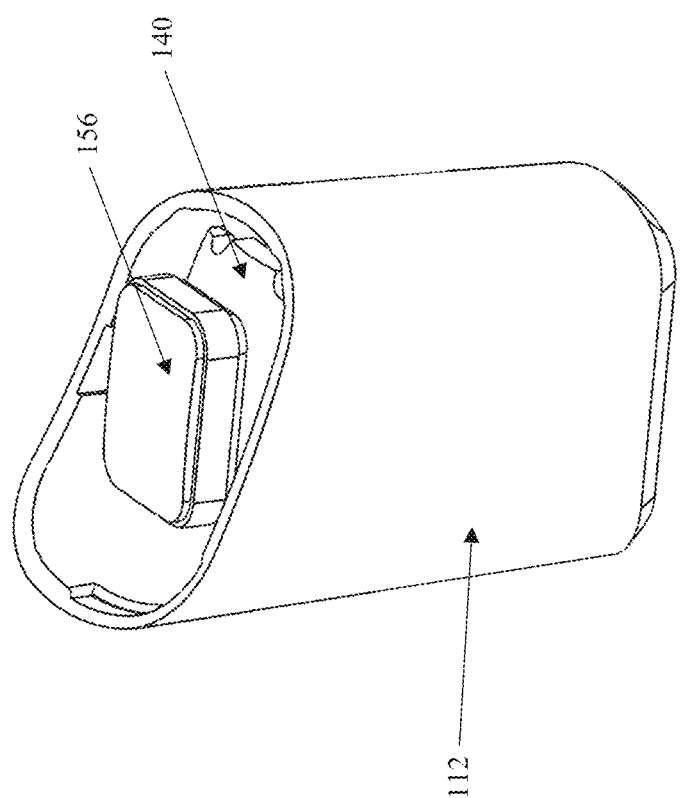
FIG. 4A is an illustration of an exemplary embodiment of a lens mechanism with a housing.
Figure 4B:
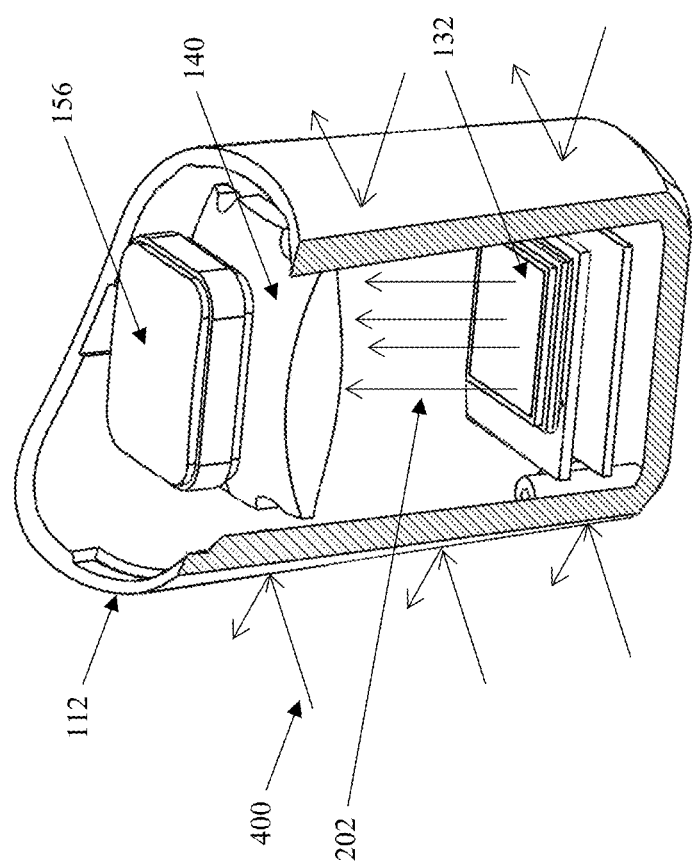
FIG. 4B is an illustration of an exemplary embodiment of a sliced internal view of a lens mechanism with a housing.

Referring now to FIG. 4A, an exemplary embodiment of a lens mechanism 100 with a housing is illustrated. In some embodiments, the lens mechanism 100 may include a housing (a first housing 112 and/or a second housing 116) that rigidly maintains components of the lens mechanism 100, such as but not limited to a lens display (a first lens display 132 and/or a second lens display 136), a display daughter board 200, a magnifying lens (a first optic 140 and/or a third optic 144), relative to one another.

Referring now to FIG. 4B, an exemplary embodiment of a sliced internal view of a lens mechanism 100 with a housing is illustrated. In some embodiments, the lens mechanism 100 may include the housing (a first housing 112 and/or a second housing 116) with lens display (a first lens display 132 and/or a second lens display 136) and a display daughter board 200 positioned at a relief height 300 from a magnifying lens (a first optic 140 and/or a third optic 144) and a prescription lens (a second optic 156 and/or a fourth optic 160) arrangement. In some embodiments, the housing (the first housing 112 and/or the second housing 116) may include opaque color such that the housing can block any ambient light 400 that interferes with the light waves 304 emitted from the lens display (the first lens display 132 and/or the second lens display 136) and reduce the quality of at least an image. As a non-limiting example, this may be useful in environments with bright lighting such as but not limited to operating rooms and factories. In some embodiments, the housing (a first housing 112 and/or a second housing 116) also protects the components of the interchangeable lens mechanism 100 from external factors such as dust, debris, and mechanical damage.

Referring now to FIG. 5, an exemplary embodiment of a relief frame (a first optic holder 148 and/or a third optic holder 152) is illustrated. In some embodiments, the relief frame (the first optic holder 148 and/or the third optic holder 152) may rigidly maintain a lens display (a first lens display 132 and/or a second lens display 136), a display daughter board 200 and a magnifying lens (a first optic 140 and/or a third optic 144) at a fixed position, with an aperture 500 for allowing light waves 304 to pass from the lens display (the first lens display 132 and/or the second lens display 136) through the magnifying lens (the first optic 140 and/or the third optic 144). In some embodiments, the relief frames (the first optic holder 148 and/or the third optic holder 152) may include screw holes 504, fixtures, and the like to dispose the relief frames to a visor 108 of a head-worn display device 104.

Referring now to FIG. 6, an exemplary embodiment of an exploded view of a lens mechanism 100 with a lens display (a first lens display 132 and/or a second lens display 136), display daughter board 200, a relief frame (a first optic holder 148 and/or a third optic holder 152), magnifying lens (a first optic 140 and/or a third optic 144) and prescription lens (a second optic 156 and/or a fourth optic 160) to detail their order in the lens mechanism 100. In some embodiments, the relief frame (the first optic holder 148 and/or the third optic holder 152) may include a plurality of snap fixtures 600 that rigidly maintain the lens display (the first lens display 132 and/or the second lens display 136), or the lens display (the first lens display 132 and/or the second lens display 136) and the daughter boards 200, relative to the relief frame (the first optic holder 148 and/or the third optic holder 152), by a hooking mechanism. In some embodiments, the snap fixtures 600 may also maintain rigid fixation with screws.

Referring now to FIG. 7, an exemplary embodiment of a prescription lens (a second optic 156 and/or a fourth optic 160) housed in a prescription lens holder (a second optic holder 120 and/or a fourth optic holder 124). In some embodiments, the lens mechanism 100 may be being rigidly held relative to one another on top by friction contact between a ledge 700 and protrusion 704 of the prescription lens (the second optic 156 and/or the fourth optic 160) and by contact with the magnifying lens (a first optic 140 and/or a third optic 144) from the bottom.

Referring now to FIG. 8, an exemplary embodiment of a head-worn display device 104 is illustrated. In some embodiments, the head-worn display device 104 may include a visor 108, nose bridge 800, earpieces 128 and lens mechanisms 100 that enables corrective stereoscopic vision of a nearby display. In some embodiments, a first housing 112 and a second housing 116 may be attached to the visor 108 that rigidly maintains their position relative to one another. In some embodiments, the first housing 112 and the second housing 116 may be angularly disposed relative to one another along a vertical plane 804 of the visor 108, and similarly an axial plane 804 running parallel to a horizon plane 904 from a user's eye looking directly forward, by an accommodation angle 808. As a non-limiting example, the accommodation angle 808 may range from zero degrees, meaning parallel, to approximately forty-five degrees.

Referring now to FIG. 9, an exemplary embodiment of a side view of a head-worn display device 104 is illustrated. In some embodiments, a first housing 112 and a second housing 116 may be disposed at a downward angle 900 relative to a horizon plane 904 of the visor 108, and similarly the horizon plane 904 of the user's eyes when looking through the visor 108. For the purposes of this disclosure, a "downward angle" is an angle that is measured from a horizontal downward to an object. As a non-limiting example, the downward angle 900 may include various ranges of angles.

Referring now to FIG. 10, an exemplary embodiment of a head-worn display device 104 with prescription lens holders of a lens mechanism 100 is illustrated. In some embodiments, prescription lens holders (a second optic holder 120 and a fourth optic holder 124) with prescription lens (a second optic 156 and a fourth optic 160) of the lens mechanism 100 may be removed or added which may enable various lens mechanism 100 to be interchanged depending on a user's preference or corrective prescriptions of the user. In some embodiments, the visor 108 may include a plurality of apertures and/or indented surfaces, where the lens mechanism 100 can be disposed. As a non-limiting example, FIG. 10 illustrates the second optic holder 120 with the second optic 156 being removed from a second surface 1000 of a visor 108 of the head-worn display device 104 and a first optic holder 148. In some embodiments, the second surface 1000 of the visor 108 of the head-worn display device 104 may include a surface of the head-worn display device 104 proximal to a user's eye. As another non-limiting example, FIG. 10 illustrates the fourth optic holder 124 with the fourth optic 160 disposed on a first surface 1004 of the visor 108 of the head-worn display device 104 and a third optic holder 152. In some embodiments, the first surface 1000 of the visor 108 of the head-worn display device 104 may include a surface of the head-worn display device 104 that is distal to the user's eye. In some embodiments, relief frames (the first optic holder 148 and the third optic holder 152), housings (a first housing 112 and a second housing 116), lens displays (a first lens display and a second lens display 136), display daughter boards 200, and magnifying lenses (a first optic 140 and a third optic 144) may be attached from a side of the visor 108 distal to the user's eyes, and the prescription lenses and prescription lens holders (a second optic holder 120 and a fourth optic holder 124) may be attached to both the visor 108 and the relief frame (the first optic holder 148 and/or the third optic holder 152), from the opposite side of the visor 108 proximal to the user's eyes utilizing screws, fixtures, or the like. In some embodiments, the prescription lenses and the prescription lens holders may be attached separately from the remainder of the components of the head-worn display device 104 such that the prescription lenses can be inter-changed and customized easily for the user without requiring substantial changes to the other components.

Referring now to FIG. 11, an exemplary embodiment of a head-worn display device 104 with an eye-line prescription lens 168 of a lens mechanism 100 is illustrated. In some embodiments, the eye-line prescription lens 168 may be connected to a top viewing area of the visor 108 that may provide a user additional corrective vision when looking above a lens display (a first lens display 132 and/or a second lens display 136) and into the surrounding environment. In another words, the eye-line prescription lenses 800 may provide additional corrective vision when the user is looking through a horizon plane 904 of the visor 108.

Referring now to FIG. 12, an exemplary embodiment of an exploded view of an eye-line prescription lens 168 of a lens mechanism 100 on a head-worn display device 104 is illustrated. In some embodiments, the eye-line prescription lens 168 may include a plurality of eye-line prescription lenses 168 and may be placed over each individual eye of a user. In some embodiments, the eye-line prescription lenses 168 may also be curved, flat, or indented in shape, and connected to the visor 108 using glue, snaps, screws, fixtures, or some combination thereof.

Referring now to FIG. 13, an exemplary embodiment of a head-worn display device 104 displaying at least an image is illustrated. In some embodiments, the at least an image may include a first image 1300 and a second image 1302. As a non-limiting example, the first image 1300 may be received from a first camera. As another non-limiting example, the second image 1302 may be received from a second camera. In some embodiments, the at least an image may include a text, image, video, animation, and the like. As a non-limiting example, as shown in FIG. 13, a first lens display 132 may display the text of the first image 1300 and a second lens display 136 may display the text of the second image 1302. In some embodiments, the at least at image may be received from a camera. As a non-limiting example, as shown in FIG. 13, the first lens display 132 may display the first image of the at least an image from the first camera where its first camera horizontal axis 1304 is angularly displaced relative the second camera horizontal axis 1308, and therefore displaying a second image of the at least an image on an angular displacement relative to a second lens display 136. This may prevent a user from seeing any stereoscopic effect or depth perception, since it is unnatural for the human eyes to be angularly displaced relative to one-another, and lead to eye strain and discomfort. A solution to this alignment problem may include to either mechanically correct the first camera so that its first camera horizontal axis 1304 is colinear with the second camera horizontal axis 1308 or perform a software correction function on the electronics module 1404 before the at least an image is sent out to the head-worn display device 104 for display. Additional disclosure related to the at least an image, the first camera, the second camera, the first camera horizontal axis 1304, the second camera horizontal axis 1308 may be found in U.S. patent application Ser. No. 18/129,601, filed on Mar. 31, 2023, entitled "FLEXIBLE AND TENSIONED CAMERA APPARATUS WITH ELECTRONIC MODULE SYSTEM FOR ENABLING MANEUVERABLE STEREOCSCOPIC FILED OF VIEW," the entirety of which is incorporated as reference.

Figure 14A:
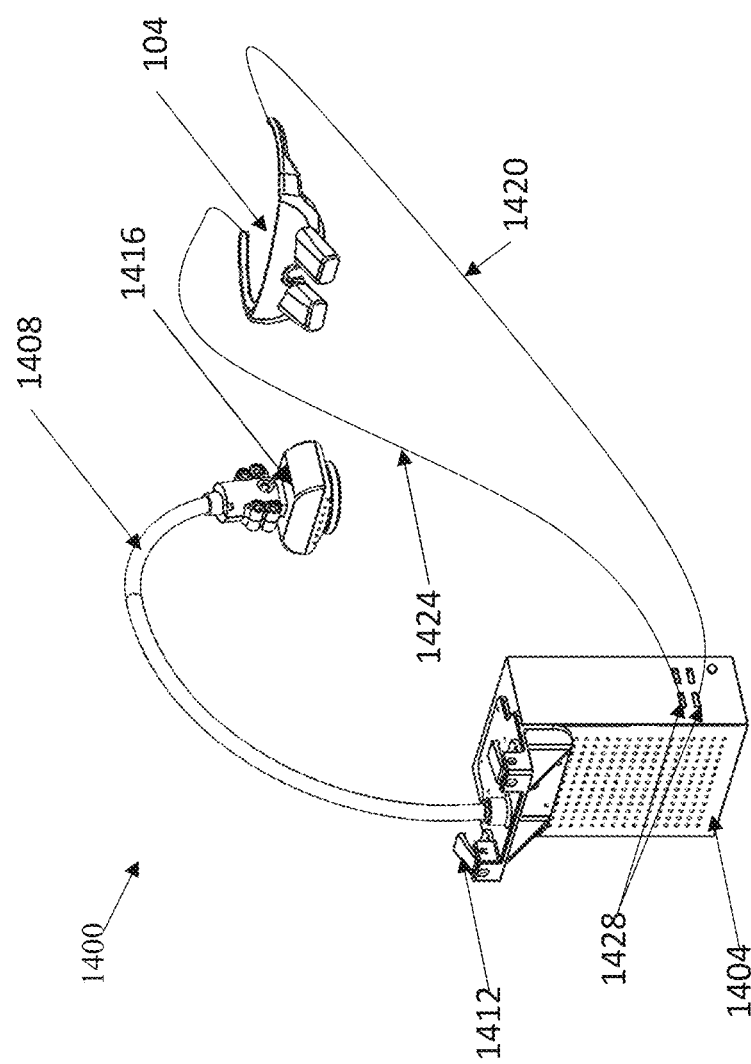
FIG. 14A is an illustration of an exemplary embodiment of a head-worn display device wired to a camera module.

Referring now to FIG. 14A, an exemplary embodiment of a head-worn display device 104 wired to a camera module (also called camera) 1400 is illustrated. In some embodiments, the camera may be configured to enable maneuverable stereoscopic field of view. A "stereoscopic field of view," as used herein, is the viewing of an object as three-dimensional. Enabling a stereoscopic field of view may include the "stereoscopy," which as used herein, is a technique for creating or enhancing the illusion of depth in an image by means of stereopsis for binocular vision. In some embodiments, the camera module 1400 may include a plurality of cameras. As a non-limiting example, the camera module 1400 may include a first camera and a second camera. In some embodiments, the camera may include an electronics module 1404 that may be attached to an articulating arm 1408 and a plurality of clamps 1412. An "electronics module," as used herein, is set of independent units that working in tandem. An "articulating arm," as used herein, is jointed instrument or positioning device used in imaging and in therapeutic procedures. A "clamp," as sued herein," is a device used to hold item together. A clamp may include a Kant twist clamp, hose clamp, cable clamp, clasps, clips, and the like. Articulating arm 1408 may be further attached to a camera head 1416 that may be directed at an object of interest. In some embodiments, the object interest may include any objects being captured by the camera head 1416. As a non-limiting example, the object of interest may be a patient laying down of a surgical table with the camera head 1416 hanging overhead. In some embodiments, the articulating arm 1408 and the camera head 1416 may be made from a material such as a polymer, metal, ceramic, or composite thereof. In some embodiments, the camera head 1416 may be consistent with any camera disclosed in the entirety of this disclosure. In some embodiments, the camera head 1416 may include a first camera and a second camera. Additional disclosure related to the articulating arm 1408, the clamp 1412, the camera head 1416, the first camera and the second camera may be found in U.S. patent application Ser. No. 18/129,601, filed on Mar. 31, 2023, entitled "FLEX-IBLE AND TENSIONED CAMERA APPARATUS WITH ELECTRONIC MODULE SYSTEM FOR ENABLING MANEUVERABLE STEREOCSCOPIC FILED OF VIEW," the entirety of which is incorporated as reference.

With continued reference to FIG. 14A, in some embodiments, an articulating arm 1408 may include an extendable arm to move or control a camera head 1416. For example, the articulating arm 1408 may include a gas spring pneumatic arm. In some embodiments, the articulating arm 1408 may include a robotic arm to move or control the camera head 1416. For example and without limitation, the robotic arm may include an articulated arm, a six-axis arm, a collaborative robot arm, a SCARA arm, a cartesian arm, a cylindrical arm, a spherical/polar arm, a parallel/delta arm, an anthropomorphic arm, a dual-arm, and the like. In some cases, the articulating arm 1408 may be controlled by an electronics module 1404 or remotely by a remote computing device, such as but not limited to a controller operated by a user or another user (such as but not limited to a technician) during a surgery to change a field of vision of the camera head 1416.

With continued reference to FIG. 14A, a camera module may include a first glasses cable 1420, a second glasses cable 1424 and a plurality of display cable connectors 1428. In some embodiments, the glasses cables may include feeder cable or fiber optic cables. A "feeder cable," as used herein, is a type of transmission line. As a non-limiting example, types of the feeder cables may include an open wire or twin feeder, coax or coaxial cable, waveguide, planar lines, stripline, balanced lines, and the like. First glasses cable 1420 and second glasses cable 1424 may transmit corresponding at least an image from a first camera and a second camera that may have been run through a software on an electronics module 1404. The display cable connectors 1428 may serve as an interface between the electronics module 1404 and the glasses cables, and may utilize the USB, HDMI, DP, Ethernet, or other data transfer protocols. The at least an image from the first camera and the second camera may be combined in a head-worn display device 104 to produce a stereoscopic image/video data with depth perception.

Figure 14B:
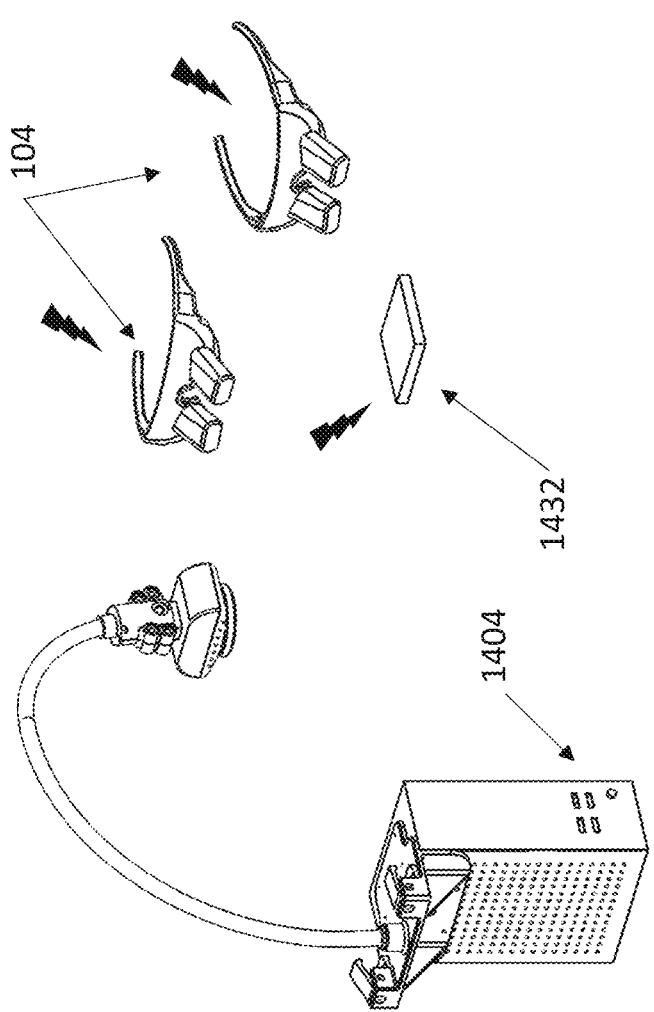
FIG. 14B is an illustration of an exemplary embodiment of a head-worn display device connected wirelessly to a console.

Referring now to FIG. 14B, an exemplary embodiment of a head-worn display device 104 connected wirelessly to a console 1432 is illustrated. In some embodiments, the console 1432 may enable local and remote stereoscopic visualization of a surgical field of view. In some embodiments, a wireless card in the electronics module 1404 may transmit at least an image from a first camera and a second camera to the console 1432. In some embodiments, the console 1432 may include a wireless router, a computer, a central processing unit, a graphics processing unit, and/or a wireless receiving card. In some embodiments, the console 1432 may perform additional software functions on the incoming image, such as white balance, de-bayering, image rotation, image alignment, compression, de-compression, packetization, or other functions before transmitting the image data to the head-worn display device 104 for display to a user or can transmit the original data with no manipulation to the head-worn display device 104 for display to the user. The at least an image from the first camera and the second camera may be combined in the head-worn display device 104 to produce a stereoscopic image/video with depth perception. In some embodiments, the console 1432 may also wirelessly send the at least an image to other displays for additional viewing options or can also connect to the interne to broadcast the at least an image to other receiving devices remotely.

Figure 15:
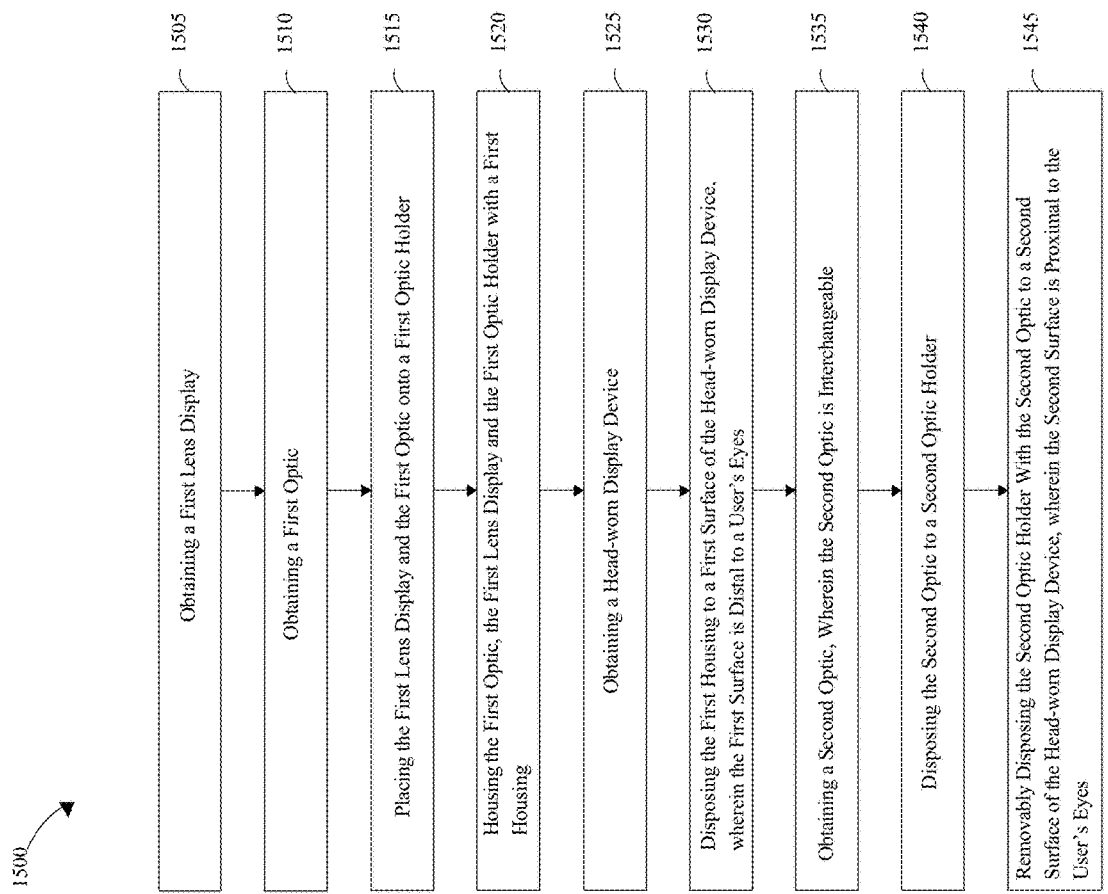
FIG. 15 is a flow diagram of an exemplary method of assembling a lens mechanism for a head-worn display device.

Referring now to FIG. 15, a flow diagram of an exemplary method 1500 of assembling a lens mechanism for a head-worn display device is illustrated. The method 1500 includes a step 1505 of obtaining a first lens display configured to emit light waves to display a first image. This may be implemented as disclosed with reference to FIGS. 1-14.

With continued reference to FIG. 15, a method 1500 includes a step 1510 of obtaining a first optic configured to magnify a first image of a first lens display. This may be implemented as disclosed with reference to FIGS. 1-14.

With continued reference to FIG. 15, a method 1500 includes a step 1515 of placing a first lens display and a first optic onto a first optic holder configured to rigidly maintain the first lens display and the first optic, wherein the first optic holder comprises an aperture configured to allow light waves to pass from the first lens display to the first optic. This may be implemented as disclosed with reference to FIGS. 1-14.

With continued reference to FIG. 15, a method 1500 includes a step 1520 of housing a first optic, a first lens display and a first optic holder with a first housing. In some embodiments, the first housing may further include a computing device, wherein the computing device may include a display daughter board. In some embodiments, the first housing may further include a computing device, wherein the computing device may include a display daughter board. This may be implemented as disclosed with reference to FIGS. 1-14.

With continued reference to FIG. 15, a method 1500 includes a step 1525 of obtaining a head-worn display device. This may be implemented as disclosed with reference to FIGS. 1-14.

With continued reference to FIG. 15, a method 1500 includes a step 1530 of disposing a first housing to a first surface of a head-worn display device, wherein the first surface is distal to a user's eyes. This may be implemented as disclosed with reference to FIG. 1-14.

With continued reference to FIG. 15, a method 1500 includes a step 1535 of obtaining a second optic configured for vision correction, wherein the second optic is interchangeable. This may be implemented as disclosed with reference to FIGS. 1-14.

With continued reference to FIG. 15, a method 1500 includes a step 1540 of disposing a second optic to a second optic holder. This may be implemented as disclosed with reference to FIGS. 1-14.

With continued reference to FIG. 15, a method 1500 includes a step 1545 of removably disposing a second optic holder with a second optic to a second surface of a head-worn display device over a first optic, wherein the second surface is proximal to a user's eyes. This may be implemented as disclosed with reference to FIGS. 1-14.

With continued reference to FIG. 15, in some embodiments, a method 1500 may further include obtaining a second lens display configured to emit light waves to display a second image, obtaining a third optic configured to magnify the second image of the second lens display, placing the second lens display and the third optic onto a third optic holder configured to rigidly maintain the second lens display and the third optic, wherein the third optic holder comprises an aperture configured to allow the light waves to pass from the second lens display to the third optic, housing the third optic, the second lens display and the third optic holder with a second housing and disposing the second housing to a first surface of a head-worn display device, wherein the first surface is distal to a user's eyes. This may be implemented as disclosed with reference to FIGS. 1-14.

With continued reference to FIG. 15, in some embodiments, a method 1500 may further include obtaining a fourth optic configured for a vision correction, wherein the fourth optic may be interchangeable, disposing the fourth optic to a fourth optic holder and removably disposing the fourth optic holder with the fourth optic to a second surface of a head-worn display device over a third optic, wherein the second surface is proximal to a user's eyes. In some embodiments, the second optic and the fourth optic may include different correction prescriptions. This may be implemented as disclosed with reference to FIGS. 1-14.

With continued reference to FIG. 15, in some embodiments, a visor of a head-worn display device may further include an eye-line prescription lens configured for a vision correction along a horizon plane of the head-worn display device. This may be implemented as disclosed with reference to FIGS. 1-14.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 16:
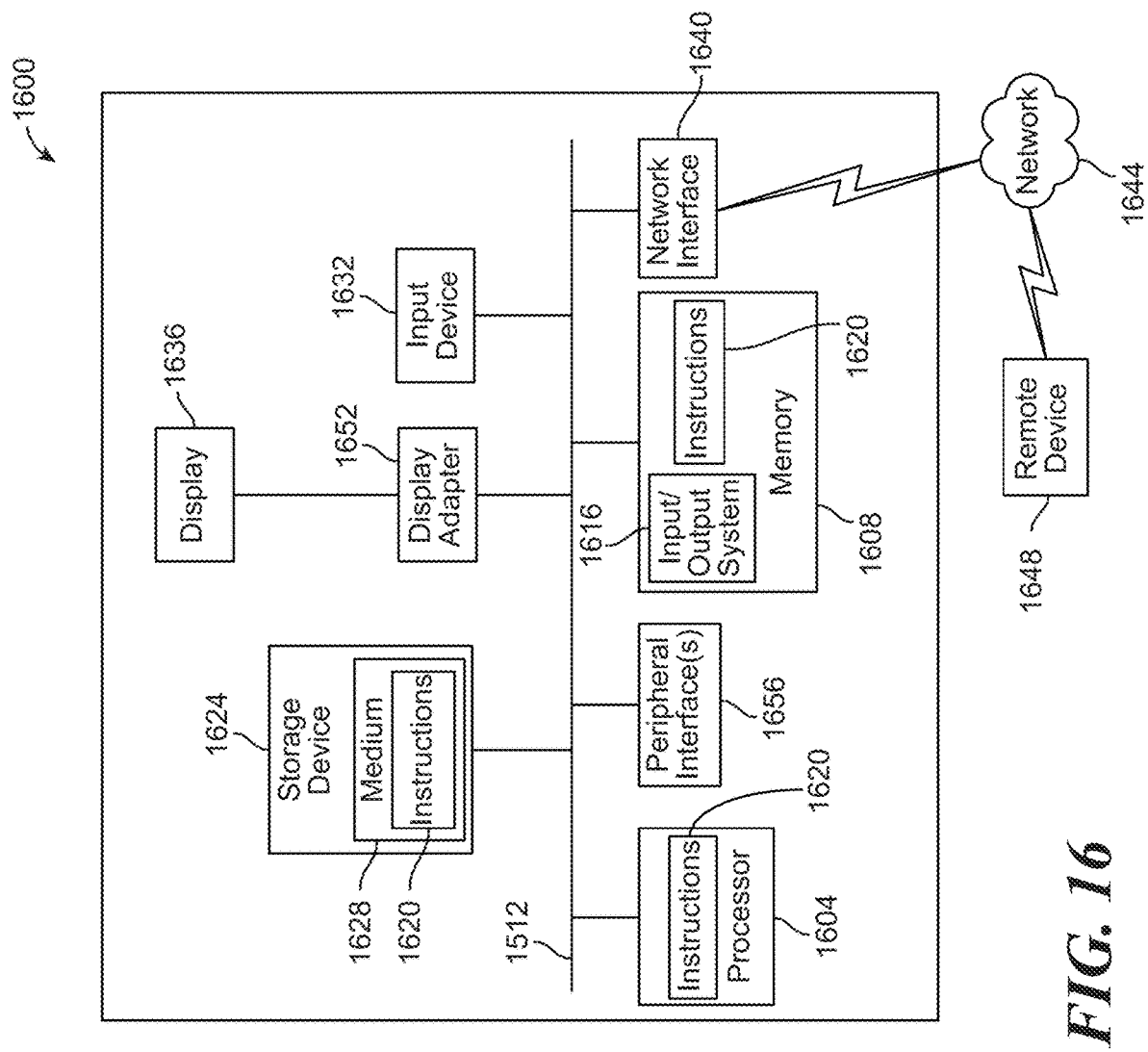
FIG. 16 is a block diagram of a computing system that can be used to implement any one or more of the methodologies disclosed herein and any one or more portions thereof.

FIG. 16 shows a diagrammatic representation of one embodiment of a computing device in the exemplary form of a computer system 1600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1600 includes a processor 1604 and a memory 1608 that communicate with each other, and with other components, via a bus 1612. Bus 1612 may include any of several types of bus structures including, but not limited to, a memory bus, a memory controller, a peripheral bus, a local bus, and any combinations thereof, using any of a variety of bus architectures.

Processor 1604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1604 may be organized according to Von Neumann and/or Harvard architecture as a non-limiting example. Processor 1604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1608 may include various components (e.g., machine-readable media) including, but not limited to, a random-access memory component, a read only component, and any combinations thereof. In one example, a basic input/output system 1616 (BIOS), including basic routines that help to transfer information between elements within computer system 1600, such as during start-up, may be stored in memory 1608. Memory 1608 may also include (e.g., stored on one or more machine-readable media) instructions (e.g., software) 1620 embodying any one or more of the aspects and/or methodologies of the present disclosure. In another example, memory 1608 may further include any number of program modules including, but not limited to, an operating system, one or more application programs, other program modules, program data, and any combinations thereof.

Computer system 1600 may also include a storage device 1624. Examples of a storage device (e.g., storage device 1624) include, but are not limited to, a hard disk drive, a magnetic disk drive, an optical disc drive in combination with an optical medium, a solid-state memory device, and any combinations thereof. Storage device 1624 may be connected to bus 1612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1624 (or one or more components thereof) may be removably interfaced with computer system 1600 (e.g., via an external port connector (not shown)). Particularly, storage device 1624 and an associated machine-readable medium 1628 may provide nonvolatile and/or volatile storage of machine-readable instructions, data structures, program modules, and/or other data for computer system 1600. In one example, software 1620 may reside, completely or partially, within machine-readable medium 1628. In another example, software 1620 may reside, completely or partially, within processor 1604.

Computer system 1600 may also include an input device 1632. In one example, a user of computer system 1600 may enter commands and/or other information into computer system 1600 via input device 1632. Examples of an input device 1632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1632 may be interfaced to bus 1612 via any of a variety of interfaces (not shown) including, but not limited to, a serial interface, a parallel interface, a game port, a USB interface, a FIREWIRE interface, a direct interface to bus 1612, and any combinations thereof. Input device 1632 may include a touch screen interface that may be a part of or separate from display 1636, discussed further below. Input device 1632 may be utilized as a user selection device for selecting one or more graphical representations in a graphical interface as described above.

A user may also input commands and/or other information to computer system 1600 via storage device 1624 (e.g., a removable disk drive, a flash drive, etc.) and/or network interface device 1640. A network interface device, such as network interface device 1640, may be utilized for connecting computer system 1600 to one or more of a variety of networks, such as network 1644, and one or more remote devices 1648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1644, may employ a wired and/or a wireless mode of communication. In general, any network topology may be used. Information (e.g., data, software 1620, etc.) may be communicated to and/or from computer system 1600 via network interface device 1640.

Computer system 1600 may further include a video display adapter 1652 for communicating a displayable image to a display device, such as display device 1636. Examples of a display device include, but are not limited to, a liquid crystal display (LCD), a cathode ray tube (CRT), a plasma display, a light emitting diode (LED) display, and any combinations thereof. Display adapter 1652 and display device 1636 may be utilized in combination with processor 1604 to provide graphical representations of aspects of the present disclosure. In addition to a display device, computer system 1600 may include one or more other peripheral output devices including, but not limited to, an audio speaker, a printer, and any combinations thereof. Such peripheral output devices may be connected to bus 1612 via a peripheral interface 1656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve a lens mechanisms and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A lens mechanism for a head-worn display device, the lens mechanism comprising:
    a first housing disposed on a head-worn display device at an angle to a horizon plane of the head-worn display device, wherein the first housing comprises:
    a first lens display, wherein the first lens display is configured to emit light waves to display a first image;
    a first optic, wherein the first optic is configured to magnify the first image of the first lens display; and
    a first optic holder configured to rigidly maintain the first lens display and the first optic,
    wherein the first optic holder comprises an aperture configured to allow the light waves to pass from the first lens display to the first optic; and
    a second optic holder, wherein:
    the second optic holder comprises a second optic configured for vision correction, wherein:
    the second optic is interchangeable; and
    the second optic is located over the first optic; and the second optic holder is configured to removably dispose the second optic to the head-worn display device; and an eye-line prescription lens, wherein the eye-line prescription lens is configured for the vision correction relative to the horizon plane.

2. The lens mechanism of claim 1, wherein the first housing further comprises a computing device, wherein the computing device comprises a display daughter board.

3. The lens mechanism of claim 2, wherein the first optic holder is further configured to rigidly maintain the computing device.

4. The lens mechanism of claim 1, wherein the first optic holder is further configured to rigidly maintain the first lens display and the first optic at a relief height (Rh).

5. The lens mechanism of claim 1, wherein the lens mechanism further comprises a second housing, wherein the second housing comprises:
a second lens display configured to emit the light waves to display a second image;
a third optic configured to magnify the second image of the second lens display; and
a third optic holder configured to rigidly maintain the second lens display and the third optic at the relief height.

6. The lens mechanism of claim 5, wherein the first housing and the second housing are further configured to block ambient light.

7. The lens mechanism of claim 5, wherein the first housing and the second housing are angularly disposed on the head-worn display device at a downward angle.

8. The lens mechanism of claim 5, wherein the first housing and the second housing are angularly disposed relative to one another along a vertical plane of the head-worn display device by an accommodation angle.

9. The lens mechanism of claim 5, wherein:
the first lens display is configured to receive the first image from a first camera; and
the second lens display is configured to receive the second an image from a second camera.

10. The lens mechanism of claim 5, wherein each of the first optic holder and the third optic holder comprises a fixture configured to rigidly maintain the first lens display and the second lens display.

11. The lens mechanism of claim 5, wherein the lens mechanism further comprises a fourth optic holder, wherein:
the fourth optic holder comprises a fourth optic, wherein the fourth optic is interchangeable and located over the third optic; and
the fourth optic holder is configured to removably dispose the fourth optic within the head-worn display device.

12. The lens mechanism of claim 11, wherein the second optic and the fourth optic comprise different correction prescriptions.

13. The lens mechanism of claim 11, wherein the third optic holder is further configured to removably dispose the third optic in the head-worn display device.

14. A method of assembling a lens mechanism for a head-worn display device, the method comprising:

obtaining a first lens display configured to emit light waves to display a first image;
obtaining a first optic configured to magnify the first image of the first lens display;
placing the first lens display and the first optic onto a first optic holder configured to rigidly maintain the first lens display and the first optic, wherein the first optic holder comprises an aperture configured to allow the light waves to pass from the first lens display to the first optic;
housing the first optic, the first lens display and the first optic holder with a first housing;
obtaining a head-worn display device having an eye-line prescription lens, wherein the eye-line prescription lens is configured for vision correction along a horizon plane of the head-worn display device;
disposing the first housing on a first surface of the head-worn display device at an angle to the horizon plane, wherein the first surface of the head-worn display device is distal to a user's eyes;
obtaining a second optic configured for vision correction, wherein the second optic is interchangeable;
disposing the second optic to a second optic holder; and
removably disposing the second optic holder with the second optic to a second surface of the head-worn display device over the first optic of the first housing, wherein the second surface of the head-worn display device is proximal to the user's eyes.

15. The method of claim 14, wherein the first housing further comprises a computing device, wherein the computing device comprises a display daughter board.

16. The method of claim 14, further comprising:
obtaining a second lens display configured to emit the light waves to display a second image;
obtaining a third optic configured to magnify the second image of the second lens display;
placing the second lens display and the third optic onto a third optic holder configured to rigidly maintain the second lens display and the third optic, wherein the third optic holder comprises the aperture configured to allow the light waves to pass from the second lens display to the third optic;
housing the third optic, the second lens display and the third optic holder with a second housing; and
disposing the second housing to the head-worn display device from the first surface of the head-worn display device.

17. The method of claim 16, further comprising:
obtaining a fourth optic configured for the vision correction, wherein the fourth optic is interchangeable;
disposing the fourth optic to a fourth optic holder; and
removably disposing the fourth optic holder with the fourth optic to the head-worn display device from the second surface of a visor of the head-worn display device, wherein the fourth optic is located over the third optic.

18. The method of claim 14, wherein the second optic and the fourth optic comprise different correction prescriptions.

* * * * *